United States Patent
Yanagi et al.

(10) Patent No.: US 6,933,101 B2
(45) Date of Patent: Aug. 23, 2005

(54) FLUORINE COMPOUND, SURFACTANT, AQUEOUS COATING COMPOSITION AND SILVER HALIDE PHOTOGRAPHIC LIGHT-SENSITIVE MATERIAL USING THEM

(75) Inventors: Terukazu Yanagi, Minami-ashigara (JP); Akira Ikeda, Minami-ashigara (JP); Nobuo Hamamoto, Minami-ashigara (JP); Takahiro Ishizuka, Minami-ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/713,041

(22) Filed: Nov. 17, 2003

(65) Prior Publication Data

US 2004/0115571 A1 Jun. 17, 2004

Related U.S. Application Data

(62) Division of application No. 10/209,946, filed on Aug. 2, 2002, now Pat. No. 6,747,169.

(30) Foreign Application Priority Data

Aug. 2, 2001 (JP) ........................................ 2001-234466

(51) Int. Cl.$^7$ .......................... G03C 1/85; G03C 1/005; G03C 1/494
(52) U.S. Cl. ......................... 430/527; 430/546; 430/631
(58) Field of Search ............................... 430/546, 527, 430/631

(56) References Cited

U.S. PATENT DOCUMENTS

| | | | | |
|---|---|---|---|---|
| 4,347,308 A | * | 8/1982 | Takeuchi et al. ............ | 430/529 |
| 5,254,448 A | * | 10/1993 | Yamada et al. ............. | 430/523 |
| 2003/0211430 A1 | * | 11/2003 | Ikeda et al. ................. | 430/523 |
| 2004/0058284 A1 | * | 3/2004 | Yoneyama et al. ......... | 430/505 |

OTHER PUBLICATIONS

Kimizuka et al., "Polymorphism in Bilayer Membranes of Novel Double–Chain Ammonium Amphiphiles", Chemistry Letters, pp. 1911–1914 (1988).

Ishikawa, Yuichi et al., "Self–Assembly of Bilayers from Double–Chain Fluorocarbon Amphiphiles in Aprotic Organic Solvents: Thermodynamic Origin and Generalization of the Bilayer Assembly", J. Am. Chem. Soc., 116, pp. 5579–5591 (1994).

Kunitake et al., Journal of the American Chemical Society, Formation and Enhanced Stability of Fluoroalkyl Bilayer Membranes, 1982, 104, pp. 5547–5549.

Nakashima et al., Journal of the American Chemical Society, Chemical Communications, Selective Binding of a Cyanine Dye at the Surface of Ammonium Bilayer Membranes, 1985, pp. 41–42.

* cited by examiner

Primary Examiner—Geraldine Letscher
(74) Attorney, Agent, or Firm—Birch, Stewart, Kolasch & Birch, LLP

(57) ABSTRACT

Disclosed is a silver halide photographic light-sensitive material having one or more layers including a light-sensitive silver halide emulsion layer on a support, wherein any of the layers contains the specific fluorine compound. The silver halide photographic light-sensitive material can be stably produced and is imparted with antistatic property.

14 Claims, No Drawings

FLUORINE COMPOUND, SURFACTANT, AQUEOUS COATING COMPOSITION AND SILVER HALIDE PHOTOGRAPHIC LIGHT-SENSITIVE MATERIAL USING THEM

This application is a Division of application Ser. No. 10/209,946 (now U.S. Pat. No. 6,747,169) filed Aug. 2, 2002 and under 35 USC §119 to JP 234466/2001 filed Aug. 2, 2001.

TECHNICAL FIELD

The present invention relates to a novel fluorine compound and surfactant that can impart surface functions such as water and oil repelling properties, antifouling property and antistatic property as well as an aqueous coating composition and silver halide photographic light-sensitive material utilizing them.

RELATED ART

Compounds having a fluorinated alkyl chain are conventionally known as surfactants. Such surfactants enables modifications of various surface properties by the unique properties of the fluorinated alkyl chain (e.g., water and oil repelling properties, lubricity, antistatic property etc.), and they are used for surface treatment of base materials of a wide range such as fibers, cloth, carpets and resins. Further, if a surfactant having a fluorinated alkyl chain (henceforth referred to as a "fluorine-containing surfactant") is added to a solution of any of various substrates in an aqueous medium, not only a uniform coating film can be formed without repellency upon coating, but also a surfactant-adsorbed layer can be formed on a substrate surface and thus the unique properties provided by the fluorinated alkyl chain can be imparted to the surface of coating.

Also in photographic light-sensitive materials, various surfactants are used and play important roles. Photographic light-sensitive materials are usually produced by separately coating a plurality of coating solutions including an aqueous solution of a hydrophilic colloid binder (e.g., gelatin) on a support to form multiple layers. Multiple hydrophilic colloid layers are often simultaneously coated as stacked layers. These layers include antistatic layer, undercoat layer, antihalation layer, silver halide emulsion layer, intermediate layer, filter layer, protective layer and so forth, and various materials for exerting functions of the layers are added to the layers. Further, polymer latex may also be added to the hydrophilic colloid layer in some cases in order to improve physical properties of film. Furthermore, in order to add functional compounds hardly soluble in water such as color couplers, ultraviolet absorbers, fluorescent brightening agents and lubricants to the hydrophilic colloid layer, these materials are sometimes emulsion-dispersed in a hydrophilic colloid solution as they are or as a solution in a high boiling point organic solvent such as phosphoric acid ester compounds and phthalic acid ester compounds for the preparation of a coating solution. As described above, photographic light-sensitive materials are generally constituted by various hydrophilic colloid layers, and in the production of them, it is required to uniformly coat coating solutions containing various materials at a high speed without defects such as repelling and uneven coating. In order to meet such requirements, a surfactant is often added to a coating solution as a coating aid.

Meanwhile, photographic light-sensitive materials are brought into contact with various materials during production, light exposure and development thereof. For example, if a light-sensitive material is in a rolled shape in process steps, a back layer formed on the back surface of the support may contact with the surface layer. Further, when it is transported during process steps, it may contact with stainless steel rollers, rubber rollers etc. When they are brought into contact with these materials, surfaces (gelatin layer) of light-sensitive materials are likely to be positively charged and they may undesirably cause discharge as the case may be. Therefore, there may remain undesirable traces of light exposure (called static marks) on the light-sensitive materials. In order to reduce this electrification property of gelatin, a compound containing a fluorine atom is effective, and a fluorine-containing surfactant is often added.

As described above, surfactants, especially fluorine-containing surfactants, are used as materials having both of the function as coating aids for providing uniformity of coated films and the function for imparting antistatic property to photographic light-sensitive materials. Specific examples thereof are disclosed in, for example, Japanese Patent Laid-open Publication (Kokai, henceforth referred to as JP-A) No. 49-46733, JP-A-51-32322, JP-A-57-64228, JP-A-64-536, JP-A-2-141739, JP-A-3-95550, JP-A-4-248543 and so forth. However, these materials do not necessarily have performance satisfying the demands for higher sensitivity and coating at higher speed required for recent photographic light-sensitive materials, and it is desired to further improve fluorine-containing surfactants. Although it is generally considered that a shorter perfluoroalkyl chain would be advantageous in degradability (degradability of compound after use), it markedly degrades orientation of the fluorinated alkyl chain on the surface of coated film. Therefore, it is strongly desired to develop a fluorine-containing surfactant that has a shorter fluoroalkyl chain and can also provide both of surface orientation (it relates to antistatic property) and uniformity of coated film.

SUMMARY OF THE INVENTION

An object of the present invention is to provide a novel fluorine compound that has a short perfluoroalkyl group, but shows superior surface orientation and enables formation of uniform coated films when used in formation of coated films, and a surfactant containing it. Another object of the present invention is to provide an aqueous coating composition that enables formation of uniform coated films having antistatic property. A further object of the present invention is to. provide a silver halide photographic light-sensitive material that can be stably produced and is imparted with antistatic property.

In order to achieve the aforementioned objects, the silver halide photographic light-sensitive material of the present invention is a silver halide photographic light-sensitive material having one or more layers including a light-sensitive silver halide emulsion layer on a support, wherein any of the layers contains a compound represented by the following formula (1).

Formula (1)

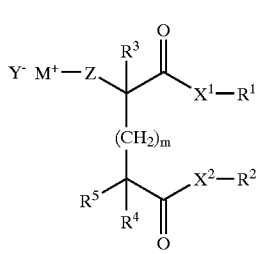

Formula (1-c)

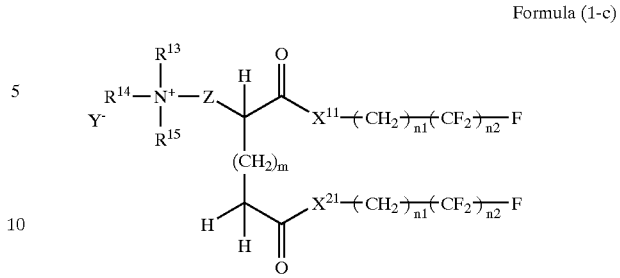

In the formula, $R^1$ and $R^2$ each represent a substituted or unsubstituted alkyl group provided that at least one of $R^1$ and $R^2$ represents an alkyl group substituted with one or more fluorine atoms. $R^3$, $R^4$ and $R^5$ each independently represent a hydrogen atom or a substituent, $X^1$, $X^2$ and Z each independently represent a divalent bridging group or a single bond, and $M^+$ represents a cationic substituent. $Y^-$ represents a counter anion, but $Y^-$ may not be present when the intramolecular charge excluding $Y^-$ is 0. m is 0 or 1.

As preferred embodiments of the present invention, there are provided the aforementioned silver halide photographic light-sensitive material, which has a light-insensitive hydrophilic colloid layer as an outermost layer and contains a compound represented by the aforementioned formula (1) in the outermost layer; and the aforementioned silver halide photographic light-sensitive material, which contains a compound represented by the aforementioned formula (1) and an anionic or nonionic surfactant in the outermost layer. As a preferred embodiment of the present invention, there is also provided the aforementioned silver halide photographic light-sensitive material, wherein the compound represented by the aforementioned formula (1) is a compound represented by the following general following formula (1-a), and as a more preferred embodiment of the present invention, there is provided the aforementioned silver halide photographic light-sensitive material, wherein the compound represented by the aforementioned formula (1) is a compound represented by the following general following formula (1-c).

Formula (1-a)

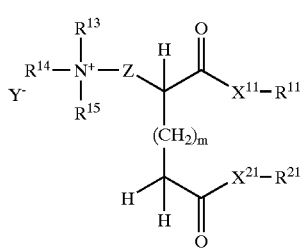

In the formula, $R^{11}$ and $R^{21}$ each represent a substituted or unsubstituted alkyl group provided that at least one of $R^{11}$ and $R^{21}$ represents an alkyl group substituted with one or more fluorine atoms and the total carbon atom number of $R^{11}$ and $R^{21}$ is 19 or less. $R^{13}$, $R^{14}$ and $R^{15}$ each independently represent a substituted or unsubstituted alkyl group and two or more of $R^{13}$, $R^{14}$ and $R^{15}$ may be taken together with the nitrogen atom to which $R^{13}$, $R^{14}$ and $R^{15}$ bond to form a ring. $X^{11}$ and $X^{21}$ each independently represent —O—, —S— or —NR$^{31}$— where $R^{31}$ represents a hydrogen atom or a substituent, and Z represents a divalent bridging group or a single bond. $Y^-$ represents a counter anion, but $Y^-$ may not be present when the intramolecular charge excluding $Y^-$ is 0. m is 0 or 1.

In the formula, $n^1$ represents an integer of 1–6 and $n^2$ represents an integer of 3–8 provided that $2(n^1+n^2)$ is 19 or less. $R^{13}$, $R^{14}$ and $R^{15}$ each independently represent a substituted or unsubstituted alkyl group and two or more of $R^{13}$, $R^{14}$ and $R^{15}$ may be taken together with the nitrogen atom to which $R^{13}$, $R^{14}$ and $R^{15}$ bond to form a ring. $X^{11}$ and $X^{21}$ each independently represent —O—, —S— or —NR$^{31}$— where $R^{31}$ represents a hydrogen atom or a substituent, and Z represents a divalent bridging group or a single bond. $Y^-$ represents a counter anion, but $Y^-$ may not be present when the intramolecular charge excluding $Y^-$ is 0. m is 0 or 1.

Further, as a preferred embodiment of the present invention, there is provided the aforementioned silver halide light-sensitive material, wherein the silver halide emulsion layer contains an emulsion in which 50% or more of total projected area of silver halide grains is provided by tabular grains having an aspect ratio of 3 or more.

In order to achieve the aforementioned objects, the present invention provides a fluorine compound represented by the aforementioned formula (1-a), a surfactant containing a compound represented by the aforementioned formula (1-a), and an aqueous coating composition containing a compound represented by the aforementioned formula (1-a).

BEST MODE FOR CARRYING OUT THE INVENTION

Hereafter, the present invention will be explained in detail. In the present specification, ranges indicated with "–" mean ranges including the numerical values before and after "–" as the minimum and maximum values.

[Fluorine Compound and Surfactant]

First, the fluorine compound and surfactant of the present invention will be explained. The fluorine compound of the present invention is represented by the aforementioned formula (1). The fluorine compound of the present invention can be used as a surfactant.

In the formula (1), $R^1$ and $R^2$ each represent a substituted or unsubstituted alkyl group provided that at least one of $R^1$ and $R^2$ represents an alkyl group substituted with one or more fluorine atoms. $R^3$, $R^4$ and $R^5$ each independently represent a hydrogen atom or a substituent, $X^1$, $X^2$ and Z each independently represent a divalent bridging group or a single bond, and $M^+$ represents a cationic substituent. $Y^-$ represents a counter anion, but $Y^-$ may not be present when the intramolecular charge excluding $Y^-$ is 0. m is 0 or 1.

In the aforementioned formula (1), $R^1$ and $R^2$ each represent a substituted or unsubstituted alkyl group. The alkyl group contains one or more carbon atoms and may be a straight, branched or cyclic alkyl group. Examples of the substituent include a halogen atom, an alkenyl group, an aryl group, an alkoxyl group, a halogen atom other than fluorine, a carboxylic acid ester group, a carbonamido group, a carbamoyl group, an oxycarbonyl group, a phosphoric acid ester group and so forth. However, at least one of $R^1$ and $R^2$ represents an alkyl group substituted with one or more fluorine atoms (an alkyl group substituted with one or more fluorine atoms is referred to as "Rf" hereafter).

Rf is an alkyl group having one or more carbon atoms and substituted with at least one fluorine atom. It is sufficient that Rf should be substituted with at least one fluorine atom, and it may have any of straight, branched and cyclic structures. It may be further substituted with a substituent other than fluorine atom or substituted with only fluorine atom or atoms. Examples of the substituent of Rf other than fluorine atom include an alkenyl group, an aryl group, an alkoxyl group, a halogen atom other than fluorine, a carboxylic acid ester group, a carboneamido group, a carbamoyl group, an oxycarbonyl group, a phosphoric acid ester group and so forth.

Rf may be a fluorine-substituted alkyl group having preferably 1–16 carbon atoms, more preferably 1–12 carbon atoms, further preferably 4–10 carbon atoms. Preferred examples of Rf include —$(CH_2)_2$—$(CF_2)_4$—F, —$(CH_2)_3$—$(CF_2)_4$—F, —$(CH_2)_2$—$(CF_2)_6$—F, —$(CH_2)_6$—$(CF_2)_4$—F, —$(CH_2)_2$—$(CF_2)_8$—F, —$CH(CF_3)_2$, —$(CH_2)$—$(CF_2)_4$—H, —$(CH_2)$—$(CF_2)_6$—H, —$(CH_2)_2$—$(CF_2)_8$—H and so forth.

Rf is more preferably an alkyl group having 4–10 carbon atoms and substituted with a trifluoromethyl group at its end, particularly preferably an alkyl group having 3–10 carbon atoms represented as —$(CH_2)_{n1}$—$(CF_2)_{n2}$—F ($n^1$ represents an integer of 1–6, and $n^2$ represents an integer of 3–8). Specific examples thereof include —$CH_2$—$(CF_2)_2$—F, —$(CH_2)_6$—$(CF_2)_4$—F, —$(CH_2)_3$—$(CF_2)_4$—F, —$CH_2$—$(CF_2)_3$—F, —$(CH_2)_2$—$(CF_2)_4$—F, —$(CH_2)_3$—$(CF_2)_4$—F, —$(CH_2)_6$—$(CF_2)_4$—F, —$(CH_2)_2$—$(CF_2)_6$—F, —$(CH_2)_3$—$(CF_2)_6$—F, —$(CH_2)_2$—$(CF_2)_6$—F and so forth. Among these, —$(CH_2)_2$—$(CF_2)_4$—F and —$(CH_2)_2$—$(CF_2)_6$—F are particularly preferred.

In the aforementioned formula (1), both of $R^1$ and $R^2$ preferably represent Rf.

When $R^1$ and $R^2$ represent an alkyl group other than Rf, i.e., an alkyl group that is not substituted with a fluorine atom, the alkyl group preferably represents a substituted or unsubstituted alkyl group having 1–24 carbon atoms, more preferably a substituted or unsubstituted alkyl group having 6–24 carbon atoms. Preferred examples of the unsubstituted alkyl group having 6–24 carbon atoms include n-hexyl group, n-heptyl group, n-octyl group, tert-octyl group, 2-ethylhexyl group, n-nonyl group, 1,1,3-trimethylhexyl group, n-decyl group, n-dodecyl group, cetyl group, hexadecyl group, 2-hexyldecyl group, octadecyl group, eicosyl group, 2-octyldodecyl, docosyl group, tetracosyl group, 2-decyltetradecyl group, tricosyl group, cyclohexyl group, cycloheptyl group and so forth. Further, preferred examples of the substituted alkyl group having a total carbon number of 6–24 include 2-hexenyl group, oleyl group, linoleyl group, linolenyl group, benzyl group, β-phenethyl group, 2-methoxyethyl group, 4-phenylbutyl group, 4-acetoxyethyl group, 6-phenoxyhexyl group, 12-phenyldodecyl group, 18-phenyloctadecyl group, 12-(p-chlorophenyl)dodecyl group, 2-(diphenyl phosphate)ethyl group and so forth.

The alkyl group other than Rf represented by $R^1$ or $R^2$ is more preferably a substituted or unsubstituted alkyl group having 6–18 carbon atoms. Preferred examples of the unsubstituted alkyl group having a carbon number of 6–18 include n-hexyl group, cyclohexyl group, n-heptyl group, n-octyl group, 2-ethylhexyl group, n-nonyl group, 1,1,3-trimethylhexyl group, n-decyl group, n-dodecyl group, cetyl group, hexadecyl group, 2-hexyldecyl group, octadecyl group, 4-tert-butylcyclohexyl group and so forth. Further, preferred examples of the substituted alkyl group having a total carbon number of 6–18 include phenethyl group, 6-phenoxyhexyl group, 12-phenyldodecyl, oleyl group, linoleyl group, linolenyl group and so forth.

The alkyl group other than Rf represented by $R^1$ or $R^2$ is particularly preferably n-hexyl group, cyclohexyl group, n-heptyl group, n-octyl group, 2-ethylhexyl group, n-nonyl group, 1,1,3-trimethylhexyl group, n-decyl group, n-dodecyl group, cetyl group, hexadecyl group, 2-hexyldecyl group, octadecyl group, oleyl group, linoleyl group or linolenyl group, most preferably a straight, cyclic or branched unsubstituted alkyl group having a carbon number of 8–16.

In the aforementioned formula (1), $R^3$, $R^4$ and $R^5$ each independently represent a hydrogen atom or a substituent. Examples of the substituent include, for example, an alkyl group having preferably 1–20 carbon atoms, more preferably 1–12 carbon atoms, particularly preferably 1–8 carbon atoms (e.g., methyl group, ethyl group, isopropyl group, tert-butyl group, n-octyl group, n-decyl group, n-hexadecyl group, cyclopropyl group, cyclopentyl group, cyclohexyl group etc.) an alkenyl group having preferably 2–20 carbon atoms, more preferably 2–12 carbon atoms, particularly preferably 2–8 carbon atoms (e.g., vinyl group, allyl group, 2-butenyl group, 3-pentenyl group etc.), an alkynyl group having preferably 2–20 carbon atoms, more preferably 2–12 carbon atoms, particularly preferably 2–8 carbon atoms (e.g., propargyl group, 3-pentynyl group etc.), an aryl group having preferably 6–30 carbon atoms, more preferably 6–20 carbon atoms, particularly preferably 6–12 carbon atoms (e.g., phenyl group, p-methylphenyl group, naphthyl group etc.), a substituted or unsubstituted amino group having preferably 0–20 carbon atoms, more preferably 0–10 carbon atoms, particularly preferably 0–6 carbon atoms (e.g., unsubstituted amino group, methylamino group, dimethylamino group, diethylamino group, dibenzylamino group etc.), an alkoxy group having preferably 1–20 carbon atoms, more preferably 1–12 carbon atoms, particularly preferably 1–8 carbon atoms (e.g., methoxy, ethoxy, butoxy etc.), an aryloxy group having preferably 6–20 carbon atoms, more preferably 6–16 carbon atoms, particularly preferably 6–12 carbon atoms (e.g., phenyloxy group, 2-naphthyloxy group etc.), an acyl group having preferably 1–20 carbon atoms, more preferably 1–16 carbon atoms, particularly preferably 1–12 carbon atoms (e.g., acetyl group, benzoyl group, formyl group, pivaloyl group etc.), an alkoxycarbonyl group having preferably 2–20 carbon atoms, more preferably 2–16 carbon atoms, particularly preferably 2–12 carbon atoms (e.g., methoxycarbonyl group, ethoxycarbonyl group etc.), an aryloxycarbonyl group having preferably 7–20 carbon atoms, more preferably 7–16 carbon atoms, particularly preferably 7–10 carbon atoms (e.g., phenyloxycarbonyl group etc.), an acyloxy group having preferably 2–20 carbon atoms, more preferably 2–16 carbon atoms, particularly preferably 2–10 carbon atoms (e.g., acetoxy group, benzoyloxy group etc.), an acylamino group having preferably 2–20 carbon atoms, more preferably 2–16 carbon atoms, particularly preferably 2–10 carbon atoms (e.g.., acetylamino group, benzoylamino group etc.), an alkoxycarbonylamino group having preferably 2–20 carbon atoms, more preferably 2–16 carbon atoms, particularly preferably 2–12 carbon atoms (e.g., methoxycarbonylamino group etc.), an aryloxycarbonylamino group having preferably 7–20 carbon atoms, more preferably 7–16 carbon atoms, particularly preferably 7–12 carbon atoms (e.g., phenyloxycarbonylamino group etc.), a sulfonylamino group having preferably 1–20 carbon atoms, more preferably 1–16 carbon atoms, particularly preferably 1–12 carbon atoms (e.g. methanesulfonylamino group, benzenesulfonylamino group etc.), a sulfamoyl group having preferably 0–20 carbon atoms, more preferably 0–16 carbon atoms, particularly preferably 0–12 carbon atoms (e.g., sulfamoyl group, methylsulfamoyl group, dimethylsulfamoyl group, phenylsulfamoyl group etc.) a carbamoyl group having preferably 1–20 carbon atoms, more preferably 1–16 carbon atoms, particularly preferably 1–12 carbon atoms (e.g., unsubstituted carbamoyl group, methylcarbamoyl group, diethylcarbamoyl group, phenylcarbamoyl group etc.), an alkylthio group having preferably 1–20 carbon atoms, more preferably 1–16 carbon atoms, particularly preferably 1–12 carbon atoms (e.g., methylthio group, ethylthio group etc.), an arylthio group having preferably 6–20 carbon atoms, more preferably 6–16 carbon atoms, particularly preferably 6–12 carbon atoms (e.g., phenylthio group etc.), a sulfonyl group having preferably 1–20 carbon atoms, more preferably 1–16 carbon atoms, particularly preferably 1–12 carbon atoms (e.g., mesyl group, tosyl group etc.), a sulfinyl group having preferably 1–20 carbon atoms, more preferably 1–16 carbon atoms, particularly preferably 1–12 carbon atoms (e.g., methanesulfinyl group, benzenesulfinyl group etc.), a ureido group having preferably 1–20 carbon atoms, more preferably 1–16 carbon atoms, particularly preferably 1–12 carbon atoms (e.g., unsubstituted ureido group, methylureido group, phenylureido group etc.), a phosphoric acid amido group having preferably 1–20 carbon atoms, more preferably 1–16 carbon atoms, particularly preferably 1–12 carbon atoms (e.g., diethylphosphoric acid amido group, phenylphosphoric acid amido group etc.), a hydroxyl group, a mercapto group, a halogen atom (e.g., fluorine atom, chlorine atom, bromine atom, iodine atom), a cyano group, a sulfo group, a carboxyl group, a nitro group, a hydroxamic acid group, a sulfino group, a hydrazino group, an imino group, a heterocyclic group having preferably 1–30 carbon atoms, more preferably 1–12, for example, such a heterocyclic group containing a hetero atom of nitrogen atom, oxygen atom, sulfur atom or the like (e.g., imidazolyl group, pyridyl group, quinolyl group, furyl group, piperidyl group, morpholino group, benzoxazolyl group, benzimidazolyl group, benzothiazolyl group etc.), a silyl group having preferably 3–40 carbon atoms, more preferably 3–30 carbon atoms, particularly preferably 3–24 carbon atoms (e.g., trimethylsilyl group, triphenylsilyl group, etc.) and so forth. These substituents may be further substituted with other substituents. Further, two or more substituents exist, they may be identical to or different from each other or one another. If possible, they may bond to each other to form a ring.

$R^3$, $R^4$ and $R^5$ preferably represent an alkyl group or a hydrogen atom, more preferably a hydrogen atom.

In the aforementioned formula, $X^1$ and $X^2$ each represent a divalent bridging group or a single bond. Although the aforementioned divalent bridging group is not particularly limited, it is preferably an arylene group, —O—, —S—, —NR$^{31}$— (R$^{31}$ represents a hydrogen atom or a substituent, the substituent may be any of the groups exemplified as substituents represented by $R^3$, $R^4$ and $R^5$, and R$^{31}$ is preferably an alkyl group, the aforementioned Rf or a hydrogen atom, more preferably a hydrogen atom) or a group consisting a combination of these groups, more preferably —O—, —S— or —NR$^{31}$—. $X^1$ and $X^2$ more preferably represent —O— or —NR$^{31}$—, further preferably —O— or —NH—, particularly preferably —O—.

In the aforementioned formula, Z represents a divalent bridging group or a single bond. Although the divalent bridging group is not particularly limited, it is preferably an alkylene group, an arylene group, —C(=O)—, —O—, —S—, —S(=O)—, —S(=O)$_2$—, —NR$^{32}$— (R$^{32}$ represents a hydrogen atom or a substituent, the substituent may be any of the groups exemplified as substituents represented by $R^3$, $R^4$ and $R^5$, and R$^{32}$ is preferably an alkyl group or a hydrogen atom, more preferably a hydrogen atom) or a group consisting a combination of these groups, more preferably an alkylene group having 1–12 carbon atoms, an arylene group 6–12 carbon atoms, —C(=O)—, —O—, —S—, —S(=O)—, —S(=O)$_2$—, —NR$^{32}$— or a group consisting a combination of the foregoing groups. Z is more preferably an alkylene group having 1–8 carbon atoms, —C(=O)—, —O—, —S—, —S(=O)—, —(=O)$_2$—, —NR$^{32}$— or a group consisting a combination of these groups, and examples thereof are —(CH$_2$)$_2$—S—, —(CH$_2$)$_2$—NH—, —(CH$_2$)$_3$—NH—, —(CH$_2$)$_2$—CO—NH—, —(CH$_2$)$_2$—S—CH$_2$—, —(CH$_2$)$_2$—NH—CH$_2$—, —(CH$_2$)$_3$—NH—CH$_2$— and so forth.

In the aforementioned formula, M$^+$ represents a cationic substituent, preferably an organic cationic substituent, more preferably an organic cationic substituent containing a nitrogen or phosphorus atom. It is further preferably a pyridinium cation or ammonium cation group, and it is particularly preferably a trialkylammonium cation group represented by the following formula (2).

Formula (2)

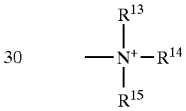

In the above formula, $R^{13}$, $R^{14}$ and $R^{15}$ each independently represent a substituted or unsubstituted alkyl group. As the substituent, those exemplified above as the substituents represented by $R^3$, $R^4$ and $R^5$ can be used. Further, if possible, two or more of $R^{13}$, $R^{14}$ and $R^{15}$ may be taken together with the nitrogen atom to which $R^{13}$, $R^{14}$ and $R^{15}$ bond to form a ring. $R^{13}$, $R^{14}$ and $R^{15}$ preferably represent an alkyl group having 1–12 carbon atoms, more preferably an alkyl group having 1–6 carbon atoms, further preferably methyl group, ethyl group or methylcarboxyl group, particularly preferably methyl group.

In the aforementioned formula, Y$^-$ represents a counter anion, and it may be an inorganic anion or an organic anion. When the charge excluding Y$^-$ is 0, there may not be Y$^-$. The inorganic anion is preferably iodide ion, bromide ion, chloride ion or the like, and the organic ion is preferably p-toluenesulfonate ion, benzenesulfonate ion, methanesulfonate ion, trifluoromethanesulfonate ion or the like. Y$^-$ is more preferably iodide ion, p-toluenesulfonate ion, or benzenesulfonate ion, particularly preferably p-toluenesulfonate ion.

In the aforementioned formula, m represents 0 or 1, preferably 0.

Among the compounds represented by the aforementioned formula (1), the compounds represented by the aforementioned formula (1-a) are preferred.

In the formula (1-a), $R^{11}$ and $R^{21}$ each represent a substituted or unsubstituted alkyl group provided that at least one of $R^{11}$ and $R^{21}$ represents an alkyl group substituted with one or more fluorine atoms and the total carbon atom number of $R^{11}$ and $R^{21}$ is 19 or less. $R^{13}$, $R^{14}$ and $R^{15}$ each independently represent a substituted or unsubstituted alkyl group and two or more of $R^{13}$, $R^{14}$ and $R^{15}$ may be taken together with the nitrogen atom to which $R^{13}$, $R^{14}$ and $R^{15}$ bond to form a ring. $X^{11}$ and $X^{21}$ each independently represent —O—, —S— or —$NR^{31}$— where $R^{31}$ represents a hydrogen atom or a substituent, and Z represents a divalent bridging group or a single bond. $Y^-$ represents a counter anion, but $Y^-$ may not be present when the intramolecular charge excluding $Y^-$ is 0. m is 0 or 1. In the formula, Z and $Y^-$ have the same meanings as defined in the aforementioned formula (1), respectively, and preferred scopes thereof are also the same as those explained for them in the formula (1). $R^{13}$, $R^{14}$, $R^{15}$ and m have the same meanings as defined in the aforementioned formula (1), respectively, and preferred scopes thereof are also the same as those explained for them in the formula (1).

In the formula, $X^{11}$ and $X^{21}$ each represent —O—, —S— or —$NR^{31}$—($R^{31}$ represents a hydrogen atom or a substituent, the substituent may be any of the groups exemplified as substituents represented by $R^3$, $R^4$ and $R^5$, and $R^{31}$ is preferably an alkyl group, the aforementioned Rf or a hydrogen atom, more preferably a hydrogen atom), more preferably —O— or —NH—, further preferably —O—.

In the aforementioned formula, $R^{11}$ and $R^{21}$ have the same meanings as $R^1$ and $R^2$ in the formula (1), respectively, and the preferred scopes thereof are also the same as those of $R^1$ and $R^2$. However, the total carbon atom number of $R^{11}$ and $R^{21}$ is 19 or less. m is 0 or 1.

Among the compounds represented by the aforementioned formula (1), the compounds represented by the following formula (1-b) are preferred.

Formula (1-b)

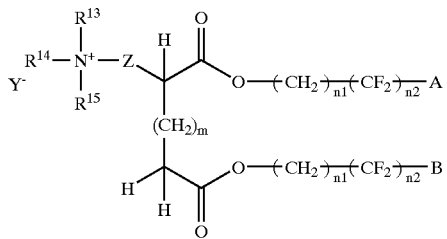

In the formula, $R^{13}$, $R^{14}$ and $R^{15}$ each independently represent a substituted or unsubstituted alkyl group and two or more of $R^{13}$, $R^{14}$ and $R^{15}$ may be taken together with the nitrogen atom to which $R^{13}$, $R^{14}$ and $R^{15}$ bond to form a ring. Z represents a divalent bridging group, and A and B each represents a fluorine atom or a hydrogen atom. $n^1$ represents an integer of 1–6 and $n^2$ represents an integer of 3–8. $Y^-$ represents a counter anion, but $Y^-$ may not be present when the intramolecular charge excluding $Y^-$ is 0. m is 0 or 1. In the formula, Z and $Y^-$ have the same meanings as defined for them in the aforementioned formula (1), respectively, and preferred scopes thereof are also the same as those explained for them in the formula (1). $R^{13}$, $R^{14}$, $R^{15}$ and m have the same meanings as defined in the aforementioned formula (1), respectively, and preferred scopes thereof are also the same as those explained for them in the formula (1). A and B preferably represent a fluorine atom.

Among the compounds represented by the aforementioned formula (1), the compounds represented by the aforementioned formula (1-c) are further preferred.

In the formula (1-C), $n^1$ represents an integer of 1–6 and $n^2$ represents an integer of 3–8 provided that $2(n^1+n^2)$ is 19 or less. $R^{13}$, $R^{14}$ and $R^{15}$ each independently represent a substituted or unsubstituted alkyl group and two or more of $R^{13}$, $R^{14}$ and $R^{15}$ may be taken together with the nitrogen atom to which $R^{13}$, $R^{14}$ and $R^{15}$ bond to form a ring. $X^{11}$ and $X^{21}$ each independently represent —O—, —S— or —$NR^{31}$— where $R^{31}$ represents a hydrogen atom or a substituent, and Z represents a divalent bridging group or a single bond. $Y^-$ represents a counter anion, but $Y^-$ may not be present when the intramolecular charge excluding $Y^-$ is 0. m is 0 or 1. In the formula, Z and $Y^-$ have the same meanings as those defined in the aforementioned formula (1), respectively, and preferred scopes thereof are also the same as those explained for them in the formula (1). $R^{13}$, $R^{14}$, $R^{15}$ and m have the same meanings as those defined in the aforementioned formula (1), respectively, and preferred scopes thereof are also the same as those explained for them in the formula (1).

$n^1$ represents an integer of 1–6, preferably an integer of 1–3, further preferably 2 or 3, most preferably 2. $n^2$ represents an integer of 3–8, more preferably 3–6, further preferably 4–6. As for preferred combination of $n^1$ and $n^2$, it is preferred that $n^1$ should be 2 or 3, and n should be 4 or 6.

Specific examples of the compounds represented by the aforementioned formula (1) are mentioned below. However, the present invention is not limited by the following examples at all. The alkyl groups and perfluoroalkyl groups mentioned in the structures of the following exemplary compounds have straight chain structures unless otherwise indicated. In addition, the abbreviations of 2EH used in the structures mean 2-ethylhexyl.

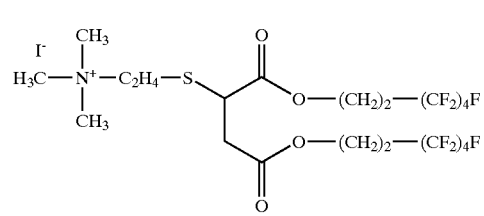

FS-1

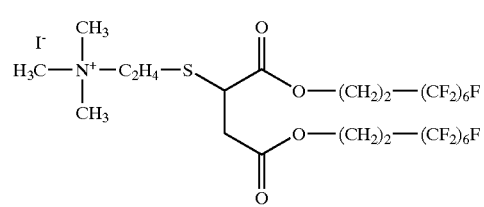

FS-2

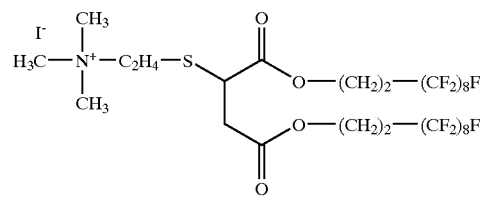

FS-3

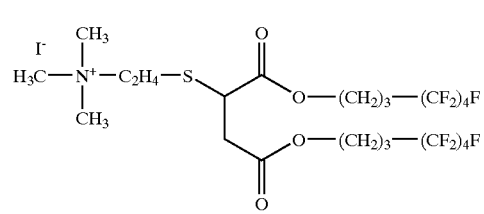

FS-4

FS-5 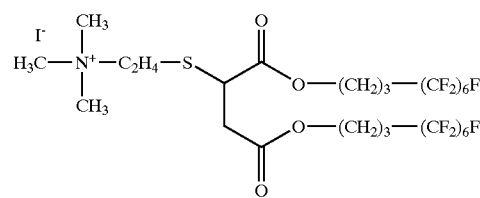
FS-6 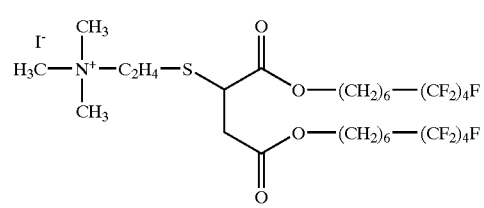
FS-7 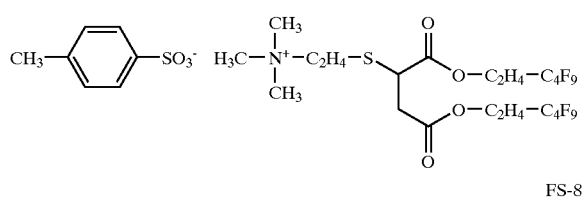
FS-8 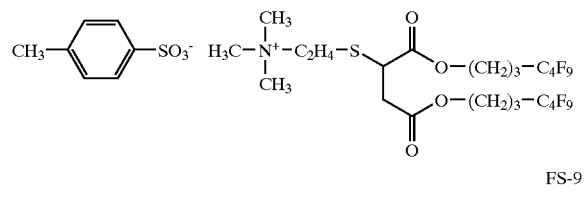
FS-9 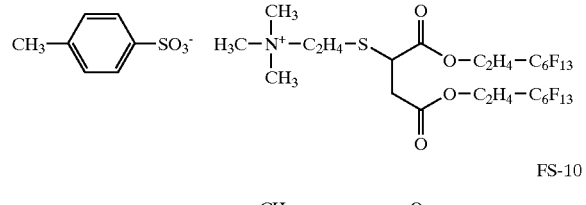
FS-10 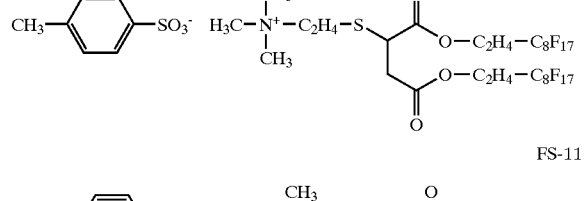
FS-11 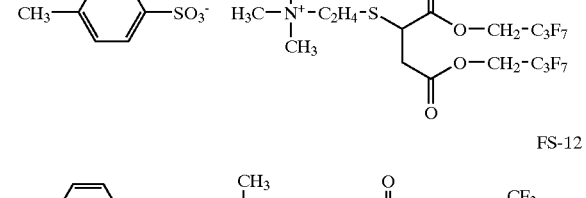
FS-12 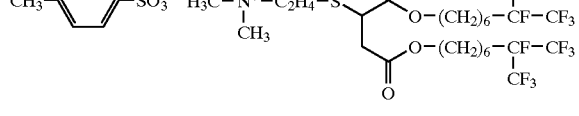
FS-13 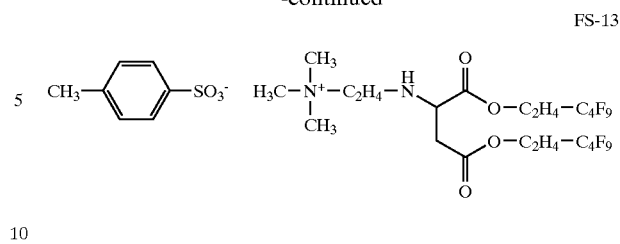
FS-14 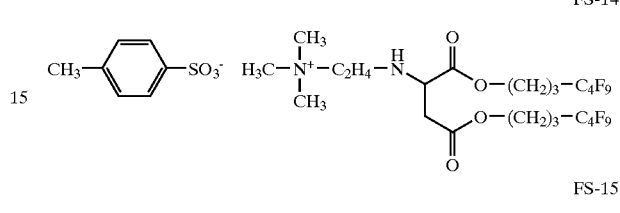
FS-15 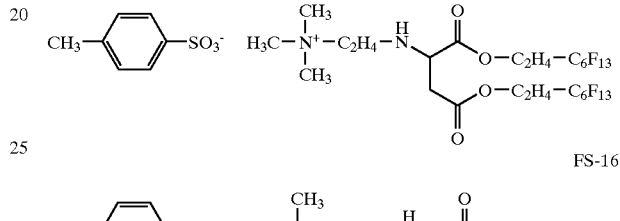
FS-16 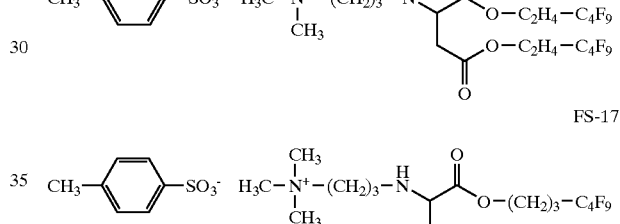
FS-17 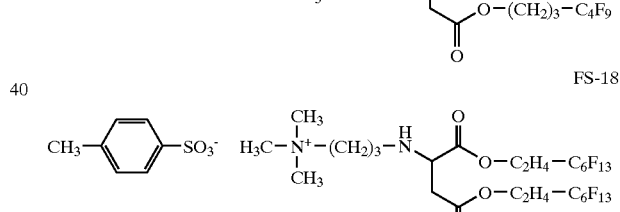
FS-18 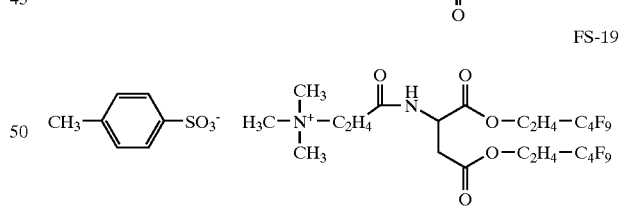
FS-19 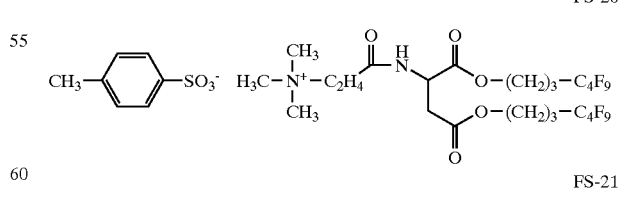
FS-20 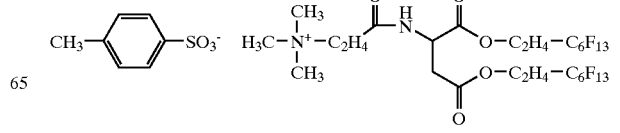
FS-21 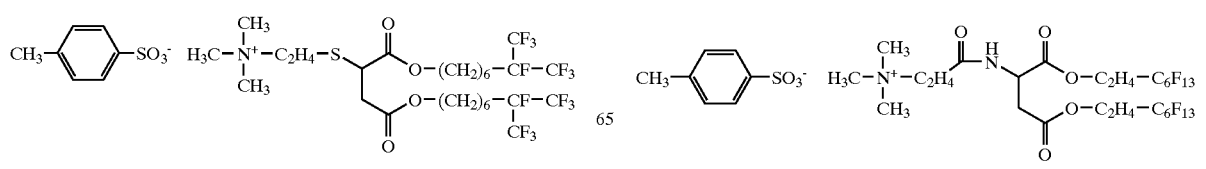

-continued

FS-22, FS-23, FS-24, FS-25, FS-26, FS-27, FS-28, FS-29, FS-30, FS-31, FS-32, FS-33, FS-34, FS-35, FS-36, FS-37

-continued
FS-38
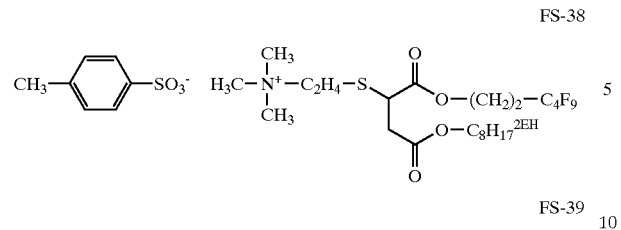
FS-39
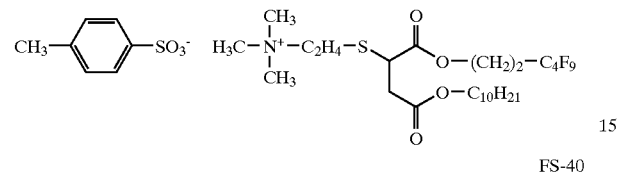
FS-40
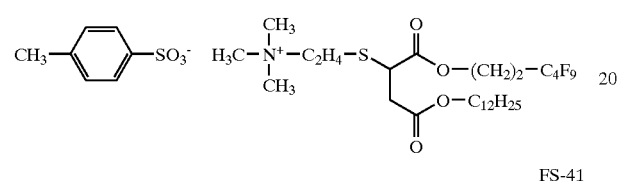
FS-41
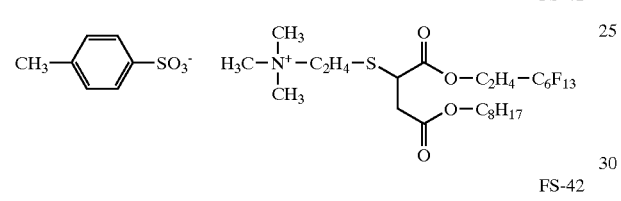
FS-42
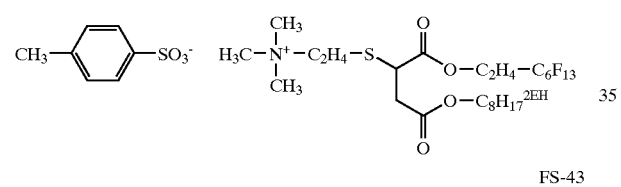
FS-43
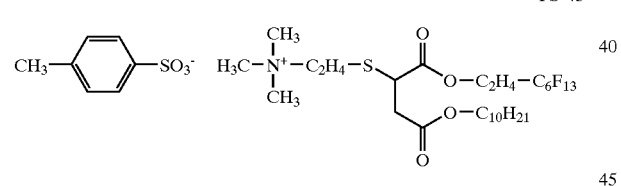
FS-44
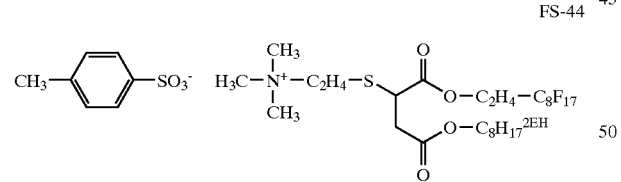
FS-45
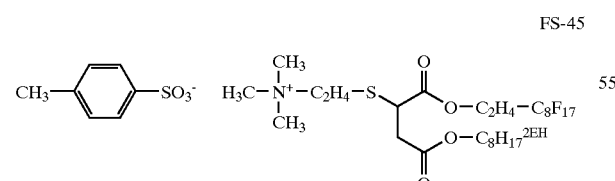
FS-46
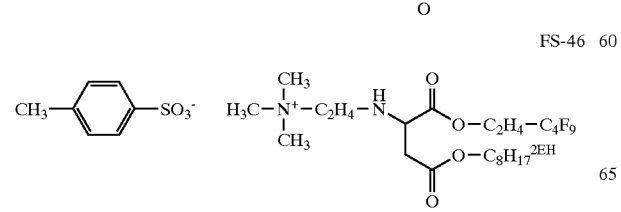
-continued
FS-47
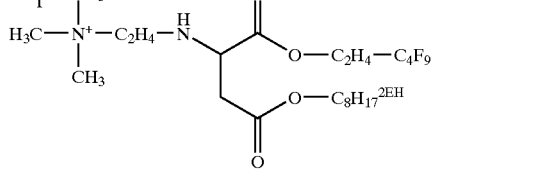
FS-48
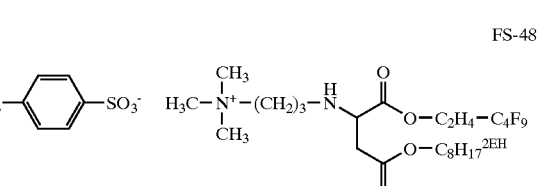
FS-49
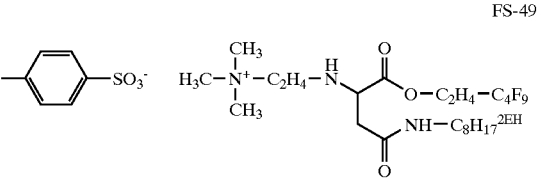
FS-50
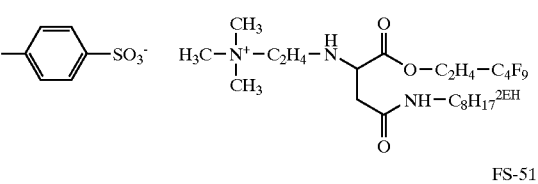
FS-51
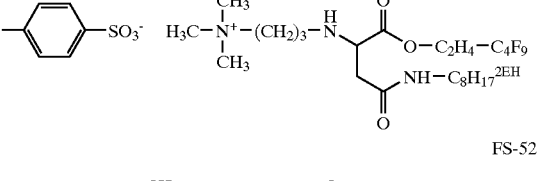
FS-52
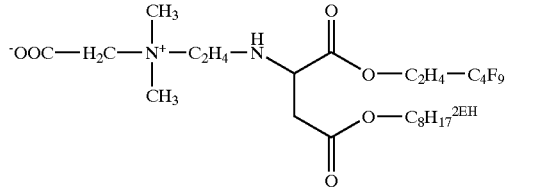
FS-53
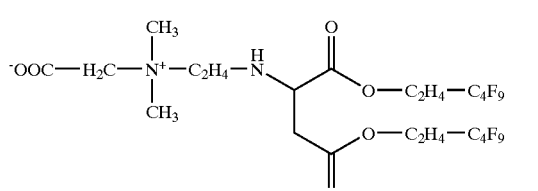
FS-54
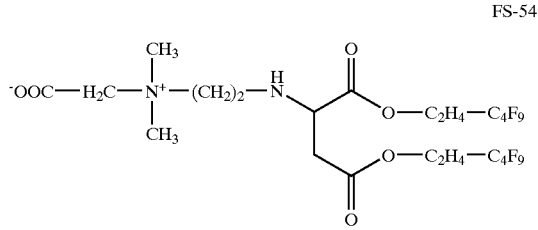

FS-55
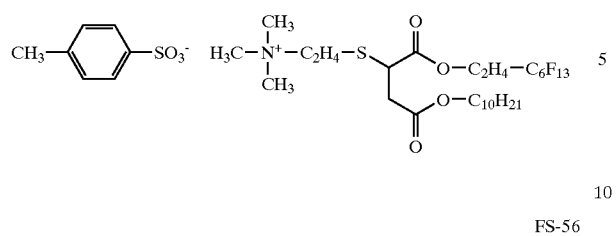
FS-56
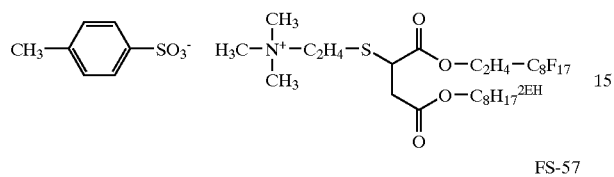
FS-57
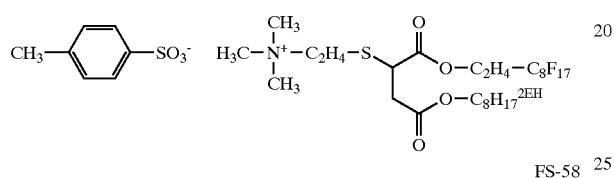
FS-58
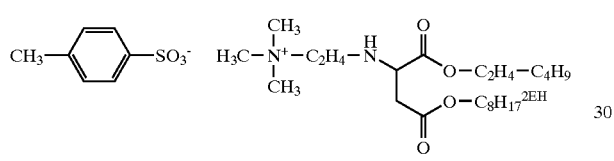
FS-59
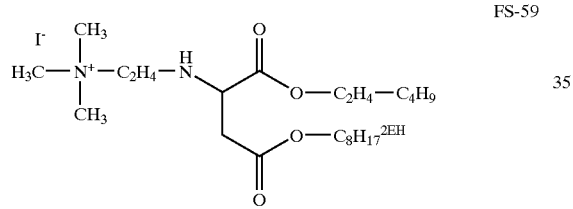
FS-60
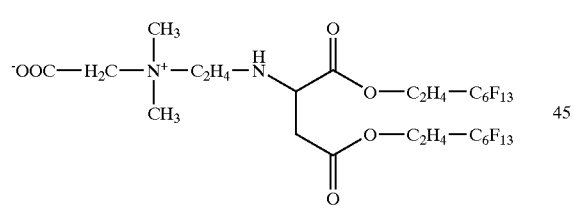
FS-61
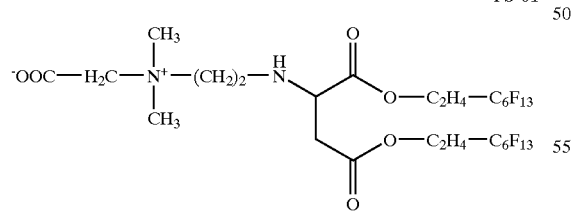
FS-62
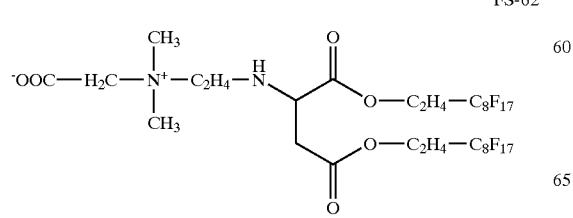
FS-63
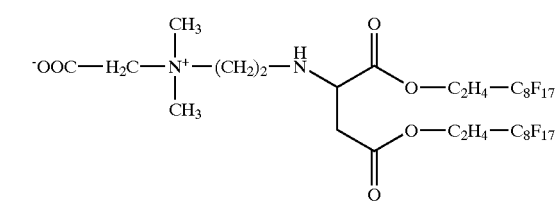
FS-64
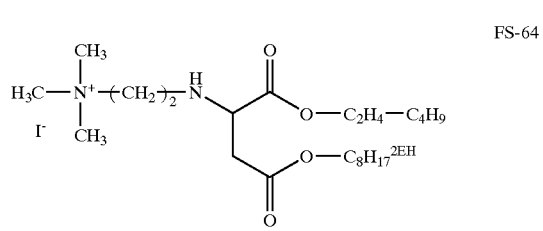
FS-65
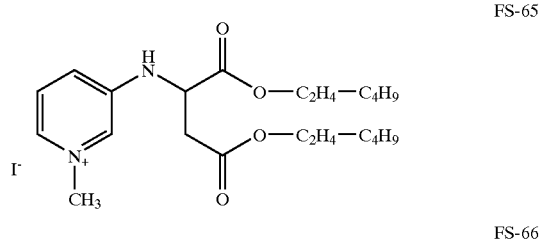
FS-66
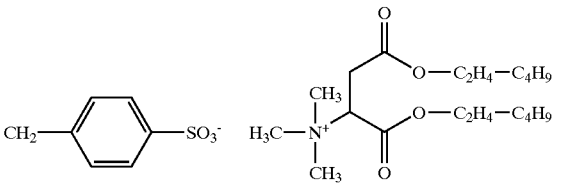
FS-67
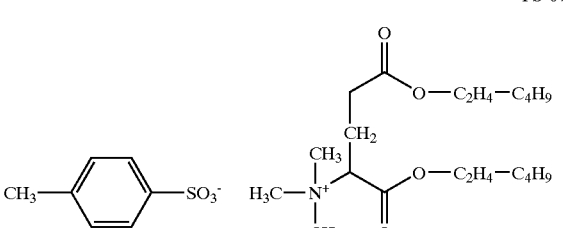
FS-68
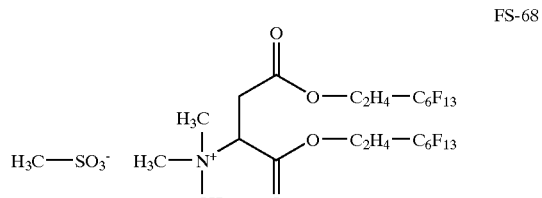
FS-69
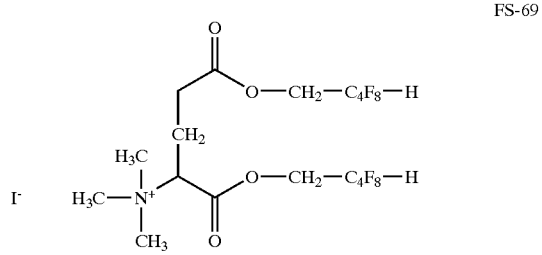

-continued

FS-70
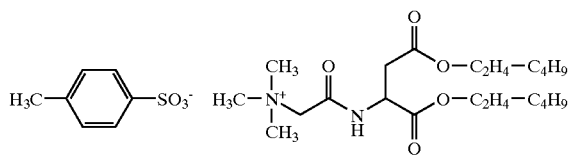

FS-71
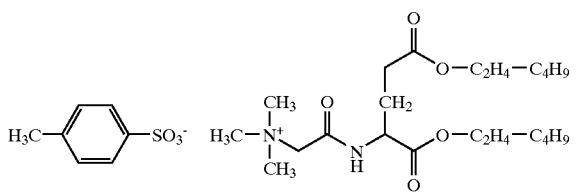

Examples of the usual synthesis method of the compounds represented by the aforementioned formulas (1), (1-a), (1-b) and (1-c) (these are also collectively referred to as "the compound of the present invention" hereinafter) are mentioned below. However, the present invention is not limited to these.

The compound of the present invention can be synthesized by using a fumaric acid derivative, maleic acid derivative, itaconic acid derivative, glutamic acid derivative, aspartic acid derivative or the like as a raw material. For example, when a fumaric acid derivative, maleic acid derivative or itaconic acid derivative is used as a raw material, the compound of the present invention can be synthesized by performing the Michael addition reaction using a nucleophilic species for a double bond of the raw material and then making the product into a cation using an alkylating agent.

[Aqueous Coating Composition]

The compound of the present invention is preferably used as surfactants in coating compositions for forming layers constituting various recording materials (in particular, silver halide photographic light-sensitive materials). Especially, it is particularly preferably used for forming a hydrophilic colloid layer as an uppermost layer of a photographic light-sensitive material, since it imparts effective antistatic ability and provides uniformity of coating. A coating composition containing the compound of the present invention as a surfactant will be explained hereafter.

The aqueous coating composition of the present invention contains the aforementioned surfactant of the present invention and a medium dissolving and/or dispersing the surfactant. In addition, depending on a purpose, other components may be suitably included.

In the aqueous coating composition of the present invention, the medium is preferably an aqueous medium. The aqueous medium includes water and a mixture of an organic solvent other than water (e.g., methanol, ethanol, isopropyl alcohol, n-butanol, methyl cellosolve, dimethylformamide, acetone etc.) with water. In the present invention, the medium of the aforementioned coating composition preferably contains 50 weight % or more of water.

In the aqueous coating composition of the present invention, a single kind of compound among the compounds of the present invention may be individually used or two or more kinds of the compounds may be used as a mixture. Further, the compound of the present invention may be used together with other surfactants. Surfactants that can be used together include various surfactants of anion type, cation type and nonion type. Moreover, the surfactants used together may be polymer surfactants, or may be fluorine-containing surfactants other than the surfactants of the present invention. The surfactants used together are more preferably anionic surfactants or nonionic surfactants. The surfactants that can be used together include, for example, those disclosed in JP-A-62-215272 (pages 649–706), Research Disclosure (RD) Items 17643, pages 26–27 (December, 1978), 18716, page 650 (November, 1979), 307105, pages 875–876 (November, 1989) and so forth.

As another component that may be contained in the aqueous coating composition of the present invention, a polymer compound can be mentioned as a typical example. The polymer compound may be a polymer soluble in an aqueous medium (henceforth referred to as "soluble polymer") or may be dispersion of a polymer in water (so-called "polymer latex"). The soluble polymer is not particularly limited, and examples thereof include, for example, gelatin, polyvinyl alcohol, casein, agar, gum arabic, hydroxyethylcellulose, methylcellulose, carboxymethylcellulose and so forth. Examples of the polymer latex include dispersions of homopolymers and copolymers of various vinyl monomers [e.g., acrylate derivatives, methacrylate derivatives, acrylamide derivatives, methacrylamide derivatives, styrene derivatives, conjugated-diene derivatives, N-vinyl compounds, O-vinyl compounds, vinylnitrile and others vinyl compounds (e.g., ethylene, vinylidene chloride)], and dispersions of condensation type polymers (e.g., polyesters, polyurethanes, polycarbonates, polyamides). Specific examples of polymer compounds of this type include the polymer compounds disclosed in JP-A-62-215272 (pages 707–763), Research Disclosure (RD) Items 17643, page 651 (December, 1978), 18716, page 650 (November, 1979), 307105, pages 873–874 (November, 1989) and so forth.

The aqueous coating composition of the present invention may contain various other compounds, and they may be dissolved or dispersed in the medium. For example, when it is used for forming a layer constituting a photographic light-sensitive material, there can be mentioned various couplers, ultraviolet absorbers, anti-color mixing agents, antistatic agents, scavengers, antifoggants, hardeners, dyes, fungicides and so forth. Further, as described above, the aqueous coating composition of the present invention is preferably used for forming a hydrophilic colloid layer as an uppermost layer of a photographic light-sensitive material, and in this case, the coating composition may contain other surfactants, matting agents, lubricants, colloidal silica, gelatin plasticizers and so forth, besides the hydrophilic colloid (e.g., gelatin) and the compound of the present invention.

The amount of the compound of the present invention is not particularly limited, and it can be arbitrarily determined depending on structure or use of a compound to be used, types and amounts of materials contained in the aqueous composition, composition of the medium and so forth. When the aqueous coating composition of the present invention is used as a coating solution for a hydrophilic colloid (gelatin) layer as an uppermost layer of a silver halide photographic light-sensitive material, for example, the concentration of the compound of the present invention is preferably 0.003–0.5 weight % in the coating composition, or preferably 0.03–5 weight % with respect to the gelatin solid content.

[Silver Halide Photographic Light-sensitive Material]

The silver halide photographic light-sensitive material of the present invention is characterized in that it has one or more layers including a light-sensitive silver halide emulsion layer on a support and any of the layers contains the compound of the present invention. In a preferred embodiment of the silver halide photographic light-sensitive material of the present invention, it has a light-insensitive hydrophilic colloid layer as an outermost layer and this outermost layer contains the compound of the present invention.

The silver halide photographic light-sensitive material of the present invention can be produced by coating one or more kinds of the aqueous coating compositions of the present invention on a support. The method for coating the coating compositions is not particularly limited, and it may be any of the slide bead coating method, slide curtain coating method, extrusion curtain coating method and extrusion bead coating method. Among these, the slide bead coating method is preferred.

Hereafter, various materials used for the silver halide photographic light-sensitive material of the present invention will be explained by exemplifying a silver halide color photographic light-sensitive material.

Silver halide grains in silver halide grain emulsion that can be used for the silver halide photographic light-sensitive material of the present invention may be those having regular crystals such as cubic, octahedral or tetradecahedral crystals, those having irregular crystals such as spherical or tabular crystals or those having crystal defects such as twinned crystal faces, or those having composite forms thereof. Tabular grains are particularly preferred.

It is preferred that, in a tabular grain emulsion, grains having an aspect ratio of 3 or more provide 50% or more of the total projected area thereof. The projected area and aspect ratio of a tabular grain can be measured from a shadowed electron micrograph of it taken together with a reference latex sphere by the carbon replica method. A tabular grain usually has a hexagonal, triangular or circular shape when viewed in a direction perpendicular to the main plane thereof, and the aspect ratio is a value obtained by dividing a diameter of a circle having the same area as the projected area of the grain (diameter as circle) with the thickness of the grain. A higher ratio of hexagon as the shape of the tabular grains is more preferred, and the ratio of the lengths of adjacent sides of the hexagon is preferably 1:2 or less.

As for the effect of the present invention, a higher aspect ratio provides more preferred photographic performance. Therefore, it is more preferred that 50% or more of the total projected area of the tabular grains in the emulsion is provided by grains having an aspect ratio of 8 or more, more preferably 12 or more. However, if the aspect ratio becomes too high, the variation coefficient of the aforementioned grain size distribution increases. Accordingly, it is usually preferred that grains should have an aspect ratio of 50 or less.

The mean grain diameter of the silver halide grains is preferably 0.2–10.0 μm, more preferably 0.5–5.0 μm, as a diameter as circle. The diameter as circle is a diameter of a circle parallel to the main plane and having the same area as the projected area of the main plane. The project area of a grain can be obtained by measuring an area of the grain on an electron microphotograph and correcting it according to magnification of the photography. A mean diameter as sphere is preferably 0.1–5.0 μm, more preferably 0.6–2.0 μm. These ranges provide the most superior relationship of sensitivity/granularity ratio of the light-sensitive emulsion. In case of tabular grains, the mean thickness thereof is preferably 0.05–1.0 μm. The mean diameter as circle used herein means an average of diameters as circle of 1000 or more grains arbitrarily collected from a uniform emulsion. The same shall apply to the mean thickness.

The silver halide grains may be monodispersed or polydispersed.

The tabular grains preferably have facing (111) main planes and side faces that connect the main planes. At least one twin plane is preferably interposed between the main planes. In the tabular grain emulsion used in the present invention, it is preferred that two twin planes are observed in each of the tabular grains. The spacing of the two twin planes can be made less than 0.012 μm as described in U.S. Pat. No. 5,219,720. Further, the value obtained by dividing the distance between (111) main planes with the twin plane spacing can be made at least 15 as described in JP-A-5-249585. In the present invention, as for the side faces connecting the facing (111) main planes of the tabular grains in the emulsion, 75% or less of the total side faces are preferably composed of (111) faces. The expression of "75% or less of the total side faces are composed of (111) faces" used herein means that crystallographic faces other than the (111) faces exist at a proportion higher than 25% of the total side faces. While such other crystallographic faces can generally be understood as being (100) faces, other faces such as (110) faces and faces with a higher index may also be included. In the present invention, if 70% or less of the total side faces are composed of (111) faces, marked effect can be obtained.

Examples of solvent for the silver halide that can be used in the present invention include (a) organic thioethers described in U.S. Pat. Nos. 3,271,157, 3,531,289, 3,574,628, JP-A-54-1019, JP-A-54-158917 etc., (b) thiourea derivatives described in JP-A-53-82408, JP-A-55-77737, JP-A-55-2982 etc., (c) silver halide solvents having a thiocarbonyl group between an oxygen atom or a sulfur atom and a nitrogen atom, described in JP-A-53-144319, (d) imidazoles described in JP-A-54-100717, (e) ammonia, (f) thiocyanates and so forth.

Particularly preferred solvents are thiocyanates, ammonia and tetramethylthiourea. The amount of the solvent to be used varies depending on the type of the solvent, and in case of thiocyanates, the amount is preferably $1 \times 10^{-4}$ mol to $1 \times 10^{-2}$ mol per mol of the silver halide.

As for the method of changing the face index of a side face of tabular grain in emulsion, EP515894A1 etc. can be referred to. The polyalkyleneoxide compounds described in U.S. Pat. No. 5,252,453 etc. can also be used. As an effective method, it is possible to use face index modifiers described in U.S. Pat. Nos. 4,680,254, 4,680,255, 4,680,256, 4,684, 607 etc. Usual photographic spectral sensitization dyes can also be used as face index modifiers similar to those mentioned above.

The silver halide emulsion can be prepared by various methods so long as it satisfies the requirements described above. In general, the preparation of a tabular grain emulsion basically includes three steps of nucleation, ripening and growth. In the nucleation step of the tabular grain emulsion used in the present invention, it is extremely effective to use gelatin with a small methionine content as described in U.S. Pat. Nos. 4,713,320 and 4,942,120, perform the nucleation at a high pBr as described in U.S. Pat. No. 4,914,014 and perform nucleation within a short time period as described in JP-A-2-222940. In the ripening step of the tabular grain emulsion, it may be effective to perform the ripening in the presence of base at a low concentration as described in U.S. Pat. No. 5,254,453 or at a high pH as described in U.S. Pat. No. 5,013,641. In the growth step of the tabular grains in the emulsion, it is particularly effective to perform the growth at a low temperature as described in U.S. Pat. No. 5,248,587 or use fine silver iodide grains as described in U.S. Pat. Nos. 4,672,027 and 4,693,964. Furthermore, it is also preferable to attain the growth by ripening with addition of silver bromide, silver iodobromide or silver chloroiodobromide fine grain emulsion. It is also possible to supply the aforementioned fine grain emulsion by using a stirring machine described in JP-A-10-43570.

The silver halide emulsion preferably contains silver iodobromide, silver iodochloride, silver bromochloride or silver iodochlorobromide. More preferably, it comprises silver iodobromide or silver iodochlorobromide. In case of silver iodochlorobromide, although the emulsion may contain silver chloride, the silver chloride content is preferably 8 mol % or less, more preferably 3 mol % or less or 0 mol %. As for the silver iodide content, since variation coefficient of the grain size distribution is preferably 25% or less, the silver iodide content is preferably 20 mol % or less. By reducing the silver iodide content, it becomes easy to make small the variation coefficient of the grain size distribution in the tabular grain emulsion. In particular, variation coefficient of grain size distribution in the tabular grain emulsion is preferably 20% or less, and the silver iodide content is preferably 10 mol % or less. Irrespective of the. silver iodide content, the variation coefficient of silver iodide content distribution among the grains is preferably 20% or less, particularly preferably 10% or less.

The silver halide emulsion preferably has a certain structure of silver iodide distribution in the grains. In this case, the structure of the silver iodide distribution may be double, triple or quadruple structure, or a structure of further higher order.

The structure of the grains in the silver halide emulsion is also preferably, for example, a triple structure consisting of silver bromide/silver iodobromide/silver bromide or a further higher order structure. The boarders of silver iodide contents in the structures may be definite borders, or the content may be changed continuously and gradually. In general, in measurement of silver iodide content using powder X-ray diffractometry, definite two peaks of different silver iodide contents are not detected, and there is obtained an X-ray diffraction profile having a portion raised along the direction to a higher silver iodide content.

Further, it is preferred that the silver iodide content is preferably higher in an internal portion than that of a surface portion, and the silver iodide content of an internal portion is higher than that of a surface portion by, preferably 5 mol % or more, more preferably 7 mol % or more.

When the silver halide emulsion comprises tabular grains, it is preferable to use tabular grains having dislocation lines. Dislocation lines in tabular grains can be observed by a direct method described in, for example, J. F. Hamilton, Phot. Sci. Eng., 11, 57 (1967) or T. Shiozawa, J. Soc. Phot. Sci. Japan, 35, 213 (1972), which is performed at a low temperature by using a transmission electron microscope. That is, silver halide grains are carefully extracted from an emulsion so as not to produce a pressure that forms dislocation lines in the grains and placed on a mesh for electron microscopic observation. The sample is observed by a transmission method while being cooled to prevent damages (e.g., print out) caused by electron rays. In this method, as the thickness of a grain increases, it becomes more difficult to transmit electron rays through it. Therefore, grains can be observed more clearly by using an electron microscope of high voltage type (200 kV or higher for a grain having a thickness of 0.25 $\mu$m). A photograph of grains obtained by this method shows positions and number of dislocation lines in each grain when the grain is viewed in a direction perpendicular to the main plane.

The average number of dislocation lines is preferably 10 or more, more preferably 20 or more, per grain. If dislocation lines are densely present or cross each other when observed, it is sometimes impossible to accurately count the number of dislocation lines per grain. Even in such cases, however, dislocation lines can be roughly counted to such an extent as in a unit of ten lines, i.e., 10 lines, 20 lines, 30 lines and so on. Accordingly, these cases can be clearly distinguished from cases where only several dislocation lines are present. The average number of dislocation lines per grain is obtained as a number average by counting the dislocation lines of 100 grains or more.

The silver halide grains can be subjected to at least one of sulfur sensitization, selenium sensitization, gold sensitization, palladium sensitization and noble metal sensitization in any steps of production of the silver halide emulsion. It is preferable to combine two or more kinds of sensitization processes. Various types of emulsions can be prepared depending on the stage at which the grains are subjected to chemical sensitization. There are a type in which chemical sensitization nuclei are embedded in the inside of the grains, a type in which the nuclei are embedded in grains at shallow positions from the surfaces and a type in which the nuclei are prepared on the surfaces of the grains. The chemical sensitization nuclei can be formed at desired sites by controlling the conditions for the preparation of emulsion depending on the purpose. However, it is preferred that at least one kind of chemical sensitization nuclei should be formed in the vicinity of the surfaces of the grains.

Chemical sensitization that can be preferably performed is chalcogenide sensitization, noble metal sensitization or a combination thereof. These types of chemical sensitization can be conducted using active gelatin as described in T. H. James, The Theory of the Photographic Process, 4th ed., pages 67 to 76, Macmillan (1977), or sulfur, selenium, tellurium, gold, platinum, palladium, iridium or a combination of multiple kinds of these sensitizers can be used at pAg of 5–10 and pH of 5–8 at a temperature of 30–80° C. as described in Research Disclosure, vol. 120, Item 12008 (April, 1974), vol. 34, Item 13452 (June, 1975), U.S. Pat. Nos. 2,642,361, 3,297,446, 3,772,031, 3,857,711, 3,901, 714, 4,266,018, 3,904,415 and British Patent 1,315,755. As for the noble metal sensitization, salts of noble metals such as gold, platinum, palladium and iridium can be used. In particular, gold sensitization, palladium sensitization or the combination of the both is preferred.

In the gold sensitization, it is possible to use known compounds such as chloroauric acid, potassium chloroaurate, potassium aurithiocyanate, gold sulfide and gold selenide. For the palladium sensitization, a divalent or tetravalent salt of palladium can be used. Preferred examples of the palladium compound used for the palladium sensitization include those represented as $R_2PdX_6$ or $R_2PdX_4$ wherein R represents a hydrogen atom, an alkali metal atom or an ammonium group and X represents a halogen atom, i.e., a chlorine, bromine or iodine atom. More specifically, $K_2PdCl_4$, $(NH_4)_2PdCl_6$, $Na_2PdCl_4$, $(NH_4)_2PdCl_4$, $Li_2PdCl_4$, $Na_2PdCl_6$ and $K_2PdBr_4$ are preferred. The gold compound and palladium compound are preferably used in combination with a thiocyanate or selenocyanate.

As the sulfur sensitizer, there can be used hypo, thiourea compounds, rhodanine compounds and sulfur-containing compounds described in U.S. Pat. Nos. 3,857,711, 4,266, 018, and 4,054,457. The chemical sensitization can also be performed in the presence of a so-called chemical sensitization aid. Examples of useful chemical sensitization aid are compounds known as those capable of suppressing fog and increasing sensitivity in the process of chemical sensitization, such as azaindene, azapyridazine and azapyrimidine. Examples of the chemical sensitization aid and modifier are described in U.S. Pat. Nos. 2,131,038, 3,411,914, 3,554,757, JP-A-58-126526 and G. F. Duffin, "Chemistry of Photographic Emulsion", pages 138–143.

It is preferable to also perform gold sensitization for the silver halide emulsion. The amount of a gold sensitizer is preferably $1 \times 10^{-4}$ to $1 \times 10^{-7}$ mol, more preferably $1 \times 10^{-5}$ to $5 \times 10^{-7}$ mol, per mol of silver halide. The amount of a palladium compound is preferably $1 \times 10^{-3}$ to $5 \times 10^{-7}$ mol, per mol of silver halide. The amount of a thiocyan compound or selenocyan compound is preferably $5 \times 10^{-2}$ to $1 \times 10^{-6}$ mol per mol of silver halide. The amount of a sulfur sensitizer used for the silver halide grains is preferably $1 \times 10^{-4}$ to $1 \times 10^{-7}$ mol, more preferably $1 \times 10^{-5}$ to $5 \times 10^{-7}$ mol, per mol of silver halide.

Selenium sensitization is a preferred sensitization technique for a silver halide emulsion. In the selenium sensitization, known unstable selenium compounds are used. Specifically, selenium compounds such as colloidal metallic selenium, selenoureas (e.g., N,N-dimethylselenourea, N,N-diethylselenourea etc.), selenoketones and selenoamides can be used. In some cases, selenium sensitization is preferably used in combination with sulfur sensitization, noble metal sensitization or both of them. For example, it is preferable to add a thiocyanate before addition of the aforementioned spectral sensitization dye and chemical sensitizer. More preferably, it is added after the formation of grains, further preferably it is added after completion of the desalting step. It is preferable to add a thiocyanate also at the time of the chemical sensitization, that is, it is preferable to add a thiocyanate twice or more times during the chemical sensitization. As the thiocyanate, there are used potassium thiocyanate, sodium thiocyanate, ammonium thiocyanate and so forth. The thiocyanate is usually added after being dissolved in an aqueous solution or a water-miscible solvent. The amount thereof is $1 \times 10^{-5}$ to $1 \times 10^{-2}$ mol, more preferably $5 \times 10^{-5}$ to $5 \times 10^{-3}$ mol, per mol of silver halide.

As a protective colloid used at the time of preparation of the silver halide emulsion or a binder of the other hydrophilic colloid layers, gelatin may be advantageously used. However, other hydrophilic binders may also be used. For example, there can be used derivatives of gelatin, graft polymers of gelatin and other polymers, proteins such as albumin and casein; cellulose derivatives such as hydroxyethylcellulose, carboxymetholcellulose and cellulose sulfate, sodium alginate, derivatives of saccharide such as derivatives of starch; various synthetic hydrophilic polymers including homopolymers and copolymers such as polyvinyl alcohol, polyvinyl alcohol partial acetal, polyvinyl-N-pyrrolidone, polyacrylic acid, polymethacrylic acid, polyacrylamide, polyvinylimidazole and polyvinylpyrazole and so forth.

As gelatin, besides lime-processed gelatin, acid-treated gelatin and enzyme-processed gelatin described in Bull. Soc. Sci. Photo. Japan. No. 16, p.30 (1966) may be used. In addition, a hydrolyzed product or an enzyme-decomposed product of gelatin can also be used.

It is preferable to wash the obtained emulsion with water for desalting and then disperse it in a newly prepared protective colloid. Although temperature of the washing with water can be selected depending on the purpose, it is preferably selected in the range of 5–50° C. Although pH for the washing can also be selected depending on the purpose, it is preferably 2–10, more preferably 3–8. The pAg for the washing is preferably 5–10, although it can also be selected depending on the purpose. The method for washing with water can be selected from noodle washing, dialysis using a semipermeable membrane, centrifugal separation, coagulation precipitation and ion exchange. As for the coagulation precipitation, there can be selected a method using a sulfate, a method using an organic solvent, a method using a water-soluble polymer, a method using a gelatin derivative or the like.

It is preferable to make a salt of metal ion exist during the preparation of the emulsion, for example, during grain formation, desalting or chemical sensitization or before coating depending on the purpose. The metal ion salt is preferably added during grain formation when it is doped into grains, or after grain formation and before the completion of chemical sensitization when it is used to modify the grain surface or used as a chemical sensitizer. It may be doped into an overall grain, or it is also possible to dope it into only a core, shell or epitaxial portion, or base grain. Examples of the metal ion include those of Mg, Ca, Sr, Ba, Al, Sc, Y, La, Cr, Mn, Fe, Co, Ni, Cu, Zn, Ga, Ru, Rh, Pd, Re, Os, Ir, Pt, Au, Cd, Hg, Tl, In, Sn, Pb, Bi and so forth. These metals can be added so long as they are in the form of a salt that can be dissolved during grain formation, such as ammonium salt, acetate, nitrate, sulfate, phosphate, hydroxy acid salt, 6-coordinated complex salt or 4-coordinated complex salt. Examples thereof are $CdBr_2$, $CdCl_2$, $Cd(NO_3)_2$, $Pb(NO_3)_2$, $Pb(CH_3COO)_2$, $K_3[Fe(CN)_6]$, $(NH_4)_4[Fe(CN)_6]$, $K_3IrCl_6$, $(NH_4)_3RhCl_6$, $K_4Ru(CN)_6$ and so forth. The ligand of the complex compounds can be selected from halo, aquo, cyano, cyanate, thiocyanate, nitrosyl, thionitrosyl, oxo and carbonyl. These metal compounds can be used either singly or as a. combination of two or more types of them.

The metal compound is preferably added after being dissolved in water or an appropriate organic solvent such as methanol or acetone. To stabilize the solution, an aqueous hydrogen halide solution (e.g., HCl and HBr) or an alkali halide (e.g., KCl, NaCl, Kbr, NaBr) can be added. It is also possible to add acid or alkali, if necessary. The metal compound can be added to a reaction vessel either before or during grain formation. Alternatively, the metal compound can be added to an aqueous solution of a water-soluble silver salt (e.g., $AgNO_3$) or an alkali halide (e.g., NaCl, KBr, KI) and continuously added during the formation of silver halide grains. Furthermore, a solution of the metal compound can be prepared separately from solutions of the water-soluble silver salt and alkali halide and continuously added in a proper period during the grain formation. Further, it is also possible to combine several different addition methods.

It is sometimes useful to use a method of adding a chalcogenide compound during the preparation of the emulsion as described in U.S. Pat. No. 3,772,031. In addition to S, Se and Te, cyanate, thiocyanate, selenocyanic acid, carbonate, phosphate and acetate can be present.

It is preferable to use an oxidizer for silver during the process of producing the emulsion. However, silver nuclei that contribute to enhancement of the sensitivity obtained by the reduction sensitization on the surface of the grain needs to remain to some extent. A compound that converts extremely fine silver grains, which are produced as a by-product in the processes of formation of silver halide grains and chemical sensitization, into silver ions is effective. The silver ions produced may form a silver salt hardly soluble in water such as silver halide, silver sulfide or silver selenide, or a silver salt easily dissolved in water such as silver nitrate.

Preferred oxidizers are inorganic oxidizers consisting of thiosulfonates and organic oxidizers consisting of quinones.

The photographic emulsion used in the present invention can contain various compounds in order to prevent fog or stabilize photographic performance during the production process, storage or photographic process of the light-sensitive material. That is, various compounds known as an antifoggant or a stabilizer can be added, and examples thereof include, for example, thiazoles such as benzothiazolium salt, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, and mercaptotetrazoles (particularly 1-phenyl-5-mercaptotetrazole); mercaptopyrimidines; mercaptotriazines; thioketo compounds such as oxadolinethione; azaindenes such as triazaindenes, tetrazaindenes (in particular, hydroxy-substituted (1,3,3a,7)-tetrazaindenes) and pentazaindenes. For example, the compounds described in U.S. Pat. Nos. 3,954,474 and 3,982,947 and Japanese Patent Publication (Kokoku, hereinafter referred to as JP-B) No. 52-28660 can be used. One class of preferred compounds are those described in JP-B-7-78597 (Japanese Patent Application No. 62-47225). The antifoggant and the stabilizer can be added at any of different times, for example, they can be added before, during and after the grain formation, during the washing with water, during dispersion after the washing, before, during and after the chemical sensitization and before coating, depending on the purpose. The antifoggant and the stabilizer can be added during preparation of the emulsion to achieve their original fog preventing effect and stabilizing effect, and in addition, they can be used for various purposes of, for example, controlling crystal habit of grains, decreasing grain size, decreasing solubility of grains, controlling chemical sensitization, controlling arrangement of dyes and so forth.

Techniques such as those for layer arrangement, silver halide emulsions, dye forming couplers, functional couplers such as DIR couplers, various additives and development usable for the emulsion and the photographic light-sensitive material using the emulsion are described in European Patent No. 0565096A1 (published on Oct. 13, 1993) and the patents cited in it. The individual items and the corresponding portions are listed below.

1. Layer structure: page 61, lines 23–35, page 61, line 41 to page 62, line 14
2. Intermediate layer: page 61, lines 36–40
3. Interlayer effect imparting layer: page 62, lines 15–18
4. Silver halide halogen composition: page 62, lines 21–25
5. Silver halide grain crystal habit: page 62, lines 26–30
6. Silver halide grain size: page 62, lines 31–34
7. Emulsion preparation method: page 62, lines 35–40
8. Silver halide grain size distribution: page 62, lines 41–42
9. Tabular grains: page 62, lines 43–46
10. Internal structures of grain: page 62, lines 47–53
11. Latent image formation type of emulsion: page 62, line 54 to page 63, line 5
12. Physical ripening and chemical ripening of emulsion: page 63, lines 6–9
13. Use of emulsion mixture: page 63, lines 10–13
14. Fogged emulsion: page 63, lines 14–31
15. Light-insensitive emulsion: page 63, lines 32–43
16. Silver coating amount: page 63, lines 49–50
17. Photographic additives: described in Research Disclosure (RD) Item 17643 (December, 1978), Item 18716 (November, 1979), and Item 307105 (November, 1989). The individual items and the corresponding portions of descriptions are mentioned below.

| Kind of Additive | RD 17643 | RD 18716 | RD 307105 |
|---|---|---|---|
| 1. Chemical sensitizer | p. 23 | p. 648, right column | p. 866 |
| 2. Sensitivity enhancing agent | | p. 648, right column | |
| 3. Spectral sensitizer and supersensitizer | pp. 23–24 | p. 648, right column to p. 649, right column | pp. 866–868 |
| 4. Brightening agent | p. 24 | p. 647, right column | p. 868 |
| 5. Antifoggant and stabilizer | pp. 24–25 | p. 649, right column | pp. 868–870 |
| 6. Light absorber, filter dye and UV absorber | pp. 25–26 | p. 649, right column to p. 650, left column | p. 873 |
| 7. Anti-staining agent | p. 25, right column | p. 650, left column to right column | p. 872 |
| 8. Dye image stabilizer | p. 25 | p. 650, left column | p. 872 |
| 9. Hardener | p. 26 | p. 651, left column | pp. 874–875 |
| 10. Binder | p. 26 | p. 651, left column | pp. 873–874 |
| 11. Plasticizer and lubricant | p. 27 | p. 650, right column | p. 876 |
| 12. Coating aid and surfactant | pp. 26–27 | p. 650, right column | pp. 875–876 |
| A part or all of these may be replaced with the compound of the present invention or they may be used in combination. | | | |
| 13. Antistatic agent | p. 27 | p. 650, right column | pp. 876–877 |
| Matting agents | | | pp. 878–879 |

18. Formaldehyde scavenger: page 64, lines 54–57
19. Mercapto type antifoggant: page 65, lines 1–2
20. Agents releasing fogging agent etc.: page 65, lines 3–7
21. Dyes: page 65, lines 7–10
22. General review for color couplers: page 65, lines 11–13
23. Yellow, magenta and cyan couplers: page 65, lines 14–25
24. Polymer coupler: page 65, lines 26–28
25. Diffusing dye forming coupler: page 65, lines 29–31
26. Colored coupler: page 65, lines 32–38
27. General review for functional couplers: page 65, lines 39–44
28. Bleaching accelerator releasing coupler: page 65, lines 45–48
29. Development accelerator releasing coupler: page 65, lines 49–53
30. Other DIR couplers: page 65, line 54 to page 66, line 4
31. Coupler diffusing method: page 66, lines 5–28
32. Antiseptic and mildew proofing agents: page 66, lines 29–33
33. Types of light-sensitive materials: page 66, lines 34–36
34. Film thickness and swelling speed of light-sensitive layer: page 66, line 40 to page 67, line 1
35. Back layer: page 67, lines 3–8
36. General review for development treatment: page 67, lines 9–11
37. Developer and developing agent: page 67, lines 12–30
38. Developer additives: page 67, lines 31–44
39. Reversal processing: page 67, lines 45–56
40. Processing solution aperture ratio: page 67, line 57 to page 68, line 12

41. Development time page 68, lines 13–15
42. Bleach fixing, bleaching and fixing: page 68, line 16 to page 69, line 31
43. Automatic processor: page 69, lines 32–40
44. Washing, rinsing and stabilization: page 69, line 41 to page 70, line 18
45. Replenishment and reuse of processing solutions: page 70, lines 19–23
46. Incorporation of developing agent into light-sensitive material: page 70, lines 24–33
47. Development temperature: page 70, lines 34–38
48. Application to film with lens: page 70, lines 39–41

The bleaching solution described in European Patent No. 602600, which contains 2-pyridinecarboxylic acid or 2,6-pyridinedicarboxylic acid, ferric salt such as ferric nitrate and persulfate, can also be preferably used. When this bleaching solution is used, it is preferable to interpose a stop step and a step of washing with water between the color development step and the bleaching step and use an organic acid such as acetic acid, succinic acid or maleic acid for a stop solution. Furthermore, for the purposes of pH adjustment and bleaching fog, the bleaching solution preferably contains 0.1–2 mol/L of an organic acid such as acetic acid, succinic acid, maleic acid, glutaric acid or adipic acid.

EXAMPLES

The present invention will be specifically explained with reference to the following examples. The materials, regents, ratios, procedures and so forth mentioned in the following examples can be optionally changed so long as such change does not depart from the spirit of the present invention. Therefore, the scope of the present invention is not limited by the following examples.

Synthesis Example 1

Synthesis of Exemplary Compound FS-1

1-1: Synthesis of 1,4-di(3,3,4,4,5,5,6,6,6-nonafluorohexyl) 2-(N,N-dimethylaminoethanethionyl)maleate In an amount of 25.1 g (41 mmol) of 1,4-di(3,3,4,4,5,5,6,6,6-nonafluorohexyl) maleate, 6.4 g (45 mmol) of N,N-di-methylaminoethanethiol hydrochloride and 5.7 g (41 mmol) of potassium carbonate were dissolved in 60 mL of N,N-dimethylformamide and stirred at 60° C. for 4 hours. Then, the reaction mixture was added with 500 mL of chloroform and the organic phase was washed with a saturated aqueous sodium hydrogencarbonate solution. Subsequently, the organic layer was collected, and the organic solvent was evaporated under reduced pressure. The residue was purified by silica gel column chromatography (hexane:ethyl acetate=8:2 to 0:10 (volume ratio)) to obtain 15.8 g (yield: 54%) of the target compound.

1-2: Synthesis of Exemplary Compound FS-1

In an amount of 5.8 g (22 mmol) of 1,4-di(3,3,4,4,5,5,6,6,6-nonafluorohexyl) 2-(N,N-dimethylaminoethanethionyl) maleate, 1.5 mL (24 mmol) of iodomethane and 60 mL of methanol were added and refluxed for 10 hours with heating. Then, the organic solvent was evaporated under reduced pressure by using an evaporator, and the residue was recrystallized form hexane/ethyl acetate (2/1 (volume ratio)) to obtain 18.9 g (yield: 100%) of the target compound (FS-1) as colorless transparent solid.

The $^1$H-NMR data of the obtained compound are as follows. $^1$H-NMR (DMSO-$d_6$): d 2.66 (m, 4H), 2.85–2.92 (m, 2H), 3.09 (m, 11H), 3.54 (d, 2H), 3.86–3.91 (m, 1H), 4.31–4.47 (m, 4H)

Example 2

Synthesis of Exemplary Compound FS-7

In an amount of 14.4 g (20 mmol) of 1,4-di(3,3,4,4,5,5,6,6,6-nonafluorohexyl) 2-(2-(N,N-dimethylamino)ethanethionyl)succinate, 3.8 g (20 mmol) of methyl p-toluenesulfonate and 60 mL of methanol were added and refluxed for 2 hours with heating. Then, the organic solvent was evaporated under reduced pressure by using an evaporator, and the residue was recrystallized from ethyl acetate. The obtained solid was dried at 80° C. for 2 hours under reduced pressure to obtain 15.3 g (yield: 85%) of the target compound (FS-7) as colorless transparent solid.

The $^1$H-NMR data of the obtained compound are as follows. $^1$H-NMR (DMSO-$d_6$): d 2.51 (s, 3H), 2.86 (br, 4H), 2.92 (m, 2H), 3.04 (m, 2H), 3.08 (s, 9H) 3.55 (m, 2H), 3.90 (dd, 1H), 4.33–4.60 (m, 4H), 7.11 (d, 2H), 7.48 (d, 2H)

Example 3

Synthesis of Exemplary Compound FS-13

3-1: Synthesis of 1,4-di(3,3,4,4,5,5,6,6,6-nonafluorohexyl) 2-(2-(N,N-dimethylamino)ethylamino)succinate In an amount of 12.0 g (20 mmol) of 1,4-di(3,3,4,4,5,5,6,6,6-nonafluorohexyl)succinate, 1.9 g (22 mmol) of N,N-dimethylaminoethylamine and 2.9 g (22 mmol) of potassium carbonate were dissolved in 50 mL of acetonitrile and refluxed for 6 hours with heating. Then, the reaction mixture was transferred to a separatory funnel and added with 500 mL of ethyl acetate. The organic phase was washed with a saturated aqueous sodium hydrogencarbonate solution. Then, the organic layer was collected, and the organic solvent was evaporated under reduced pressure. The residue was purified by silica gel column chromatography (chloroform:methanol=100:3 to 100:6 (volume ratio)) to obtain 10.7 g (yield: 54%) of the target compound.

3-2: Synthesis of FS-13

In an amount of 10.7 g (15 mmol) of the above compound, 2.9 g (15 mmol) of methyl p-toluenesulfonate and 40 mL of methanol were added and refluxed for 2 hours with heating. Then, the organic solvent was evaporated under reduced pressure by using an evaporator, and the residue was recrystallized from ethyl acetate. The obtained solid was dried at 80° C. for 2 hours under reduced pressure to obtain 10.0 g (yield: 74%) of the target compound (FS-13) as colorless transparent solid.

The $^1$H-NMR data of the obtained compound are as follows. $^1$H-NMR (DMSO-$d_6$): d 2.50 (s, 3H), 2.61–2.73 (br, 8H), 3.07 (s, 9H), 3.33 (m, 2H), 3.66 (m, 1H), 4.30–4.40 (m, 4H), 7.11 (d, 2H), 7.48 (d, 2H)

Example 4

Synthesis of Exemplary Compound FS-16

4-1: Synthesis of 1,4-di(3,3,4,4,5,5,6,6,6-nonafluorohexyl) 2-(3-(N,N-dimethylamino)propylamino)succinate In an amount of 30.0 g (49 mmol) of 1,4-di(3,3,4,4,5,5,6,6,6-nonafluorohexyl)maleate, 6.8 mL (54 mmol) of N,N- dimethylaminopropylamine and 7.5 g (54 mmol) of potassium carbonate were dissolved in 120 mL of acetonitrile and refluxed for 6 hours with heating. Then, the reaction mixture was transferred to a separatory funnel and added with 1000 mL of ethyl acetate. The organic phase was washed with a saturated aqueous sodium hydrogencarbonate solution. Then, the organic layer was collected, and the organic solvent was evaporated under reduced pressure. The residue was purified by silica gel column chromatography (chloroform:methanol 100:3 (volume ratio)) to obtain 2.64 g (yield: 75%) of the target compound as a brown oily compound.

4-2: Synthesis of FS-16

In an amount of 26.4 g (37 mmol) of the above compound, 6.92 g (37 mmol) of methyl p-toluenesulfonate and 100 mL of methanol were added and refluxed for 2 hours with heating. Then, the organic solvent was evaporated under reduced pressure by using an evaporator to obtain 33.3 g (yield: 100%) of the target compound (FS-16) as a yellow tarry compound.

The $^1$H-NMR data of the obtained compound are as follows. $^1$H-NMR (DMSO-$d_6$): d 1.82 (br, 2H), 2.50 (s, 3H), 2.62–2.76 (br, 8H), 3.04 (s, 9H) 3.33 (br, 2H), 3.65 (br, 1H), 4.32–4.39 (m, 4H), 7.11 (d, 2H), 7.48 (d, 2H)

Example 5

Synthesis of Exemplary Compound FS-47

In an amount of 20.0 g (42 mmol) of 1-mono(2-ethylhexyl) 4-mono(3,3,4,4,5,5,6,6,6-nonafluorohexyl) maleate, 4.0 g (46 mmol) of N,N-dimethylaminoethylamine and 5.8 g (42 mmol) of potassium carbonate were dissolved in 60 mL of N,N-dimethylformamide and stirred at 60° C. for 12 hours. Then, the reaction mixture was added with 500 mL of chloroform and the organic phase was washed with a saturated aqueous sodium hydrogencarbonate solution. Subsequently, the organic layer was collected, and the organic solvent was evaporated under reduced pressure. The residue was purified by silica gel column chromatography (chloroform:methanol=98:2 (volume ratio)) to obtain 15.9 g (yield: 67%) of an oily compound. Then, the compound was added with 60 mL of methanol and 1.9 mL (31 mmol) of iodomethane and refluxed for 8 hours with heating. Subsequently, the organic solvent was evaporated under reduced pressure by using an evaporator to obtain 19.9 g (yield: 67%) of the target compound as a yellow waxlike compound.

The $^1$H-NMR data of the obtained compound are as follows. $^1$H-NMR (DMSO-$d_6$): d 0.83 (m, 6H), 1.20 (m, 8H), 1.53 (m, 1H), 2.61–2.97 (m, 6H), 2.90 (br, 1H), 3.09 (s, 9H), 3.17 (s, 1H), 3.30 (m, 2H), 3.66 (m, 1H), 4.02 (m, 2H), 4.35 (t, 2H)

Example 6

Synthesis of Exemplary Compound FS-64

In an amount of 35.5 g (75 mmol) of 1-mono(2-ethylhexyl) 4-mono(3,3,4,4,5,5,6,6,6-nonafluorohexyl) maleate, 11.7 g (82 mmol) of N,N-dimethylaminoethanethiol hydrochloride and 10.4 g (75 mmol) of potassium carbonate were dissolved in 60 mL of N,N-dimethylformamide and stirred at 60° C. for 4 hours. Then, the reaction mixture was added with 500 mL of chloroform and the organic phase was washed with a saturated aqueous sodium hydrogencarbonate solution.

Subsequently, the organic layer was collected, and the organic solvent was evaporated under reduced pressure. Then, the residue was added with 100 mL of methanol and 4.7 mL (75 mmol) of iodomethane and refluxed for 8 hours with heating. Thereafter, the organic solvent was evaporated under reduced pressure by using an evaporator, and the residue was recrystallized from (hexane:ethyl acetate=2:1 (volume ratio)) to obtain 49.7 g (yield: 92%) of the target compound as a yellow waxlike compound.

The $^1$H-NMR data of the obtained compound are as follows. $^1$H-NMR (DMSO-$d_6$): d 0.83 (m, 6H), 1.29 (m, 8H), 1.52 (m, 1H), 2.64 (m, 2H), 2.84–2.91 (m, 2H), 3.09 (s, 9H), 3.16 (d, 2H) 3.56 (m, 2H), 3.85 (dd, 1H), 4.01 (m, 2H), 4.36 (br, 2H)

Example 7

Synthesis of Exemplary Compound FS-70

7-1: Synthesis of 1,4-di(3,3,4,4,5,5,6,6,6-nonafluorohexyl)aspartate

In an amount of 10.0 g (80 mmol) of aspartic acid, 44.3 g (163 mmol) of 3,3,4,4,5,5,6,6,6-nonafluorohexanol and 18.2 g (96 mmol) of p-toluenesulfonic acid monohydrate were dissolved in 400 mL of toluene and stirred at 120° C. for 15 hours. Then, the reaction mixture was cooled to room temperature, and the deposited crystals were collected by filtration, added with 500 mL of ethyl acetate and a saturated aqueous sodium hydrogencarbonate solution to wash the organic phase. Then, the organic layer was collected, and the organic solvent was evaporated under reduced pressure to obtain 35.5 g (yield: 76%) of the target compound as a yellow oily compound.

7-2: Synthesis of 1,4-di(3,3,4,4,5,5,6,6,6-nonafluorohexyl) N-(N',N'-dimethylaminomethylcarbonyl)aspartate In an amount of 8.2 g (13.1 mmol) of 1,4-di(3,3,4,4,5,5,6,6,6-nonafluorohexyl)aspartate, 1.35 g of (13.1 mmol) of N,N-dimethylglycine and 2.76 g (1.43 mmol) of 1-ethyl-3-(3-dimethylaminopropyl)carbodiimide hydrochloride (henceforth referred to as "WSC") were dissolved in 50 mL of dimethylformamide, stirred at 50° C. for 2 hours, then added with ethyl acetate and added with a saturated aqueous sodium hydrogencarbonate solution to wash the organic phase. Then, the organic layer was collected, and the organic solvent was evaporated under reduced pressure. The residue was purified by silica gel column chromatography (hexane:ethyl acetate=2:8 (w/w)) to obtain 5.6 g (yield: 60%) of the target compound as a yellow oily compound.

7-3: Synthesis of FS-70

In an amount of 5.6 g (7.9 mmol) of the above oily compound, 1.47 g (7.9 mmol) of methyl p-toluenesulfonate and 25 mL of methanol were added and refluxed for 6 hours with heating. Then, the organic solvent was evaporated under reduced pressure by using an evaporator to obtain 6.9 g (yield: 99%) of the target compound (FS-70) as a yellow tarry compound.

The $^1$H-NMR data of the obtained compound are as follows. $^1$H-NMR (DMSO-$d_6$): d 2.29 (s, 3H), 2.56–2.78 (m, 4H), 2.85 (d, 2H), 3.21 (s, 9H), 4.15 (s, 2H), 4.31–4.40 (m, 4H), 4.73 (m, 1H), 7.10 (d, 2H), 7.48 (d, 2H), 9.11 (d, 1H)

Example 8

Synthesis of Exemplary Compound FS-71

8-1: Synthesis of 1,5-di(3,3,4,4,5,5,6,6,6-nonafluorohexyl) glutamate p-toluenesulfonic Acid Salt In an amount of 14.7 g (0.1 mol) of glutamic acid, 58.2 g (0.22 mol) of 3,3,4,4,5,5,6,6,6-nonafluorohexanol and 22.8 g (0.12 mol) of p-toluenesulfonic acid monohydrate were dissolved in 500 mL of toluene and stirred at 120° C. for 6 hours. Then, the reaction mixture was cooled to room temperature, and the deposited crystals were collected by filtration and dried to obtain 69.6 g (yield: 89%) of the target substance as white crystals.

8-2: Synthesis of 1,5-di(3,3,4,4,5,5,6,6,6-nonafluorohexyl) glutamate

In an amount of 15.0 g (19.2 mmol) of 1,5-di(3,3,4,4,5,5,6,6,6-nonafluorohexyl)glutamate p-toluenesulfonic acid salt and ethyl acetate were added with a saturated aqueous sodium hydrogencarbonate solution to wash the organic phase. Then, the organic layer was collected, and the organic solvent was evaporated under reduced pressure to obtain 15.0 g (yield: 74%) of the target compound as a yellow oily compound.

8-3: Synthesis of 1,5-di(3,3,4,4,5,5,6,6,6-nonafluorohexyl) N-(N'N'-dimethylaminomethylcarbonyl)glutamate In an amount of 8.31 g (13.0 mmol) of 1,5-di(3,3,4,4,5,5,6,6,6-nonafluorohexyl)glutamate, 1.40 g (13.7 mmol) of N,N-dimethylglycine and 2.74 g (1.43 mmol) of WSC were dissolved in 50 mL of dimethylformamide, stirred at 50° C. for 3 hours, added with chloroform and added with a saturated aqueous sodium hydrogencarbonate solution to wash the organic phase. Then, the organic layer was collected, and the organic solvent was evaporated under reduced pressure. The residue was purified by silica gel column chromatography (chloroform) to obtain 7.48 g (yield: 79%) of the target compounds as a yellow oily compound.

8-4: Synthesis of FS-71

In an amount of 3.4 g (4.8 mmol) of 1,5-di(3,3,4,4,5,5,6,6,6-nonafluorohexyl) N-(2-(N',N'-dimethylamino)ethyl) glutamate, 0.88 g (4.8 mmol) of methyl p-toluenesulfonate and 27 mL of methanol were added and refluxed for 9 hours with heating. Then, the reaction mixture was filtered through a Cerite layer. The filtrate was collected, and the organic solvent was evaporated under reduced pressure by using an evaporator to obtain 3.6 g (yield: 83%) of the target compound (FS-71) as a yellow tarry compound.

The $^1$H-NMR data of the obtained compound are as follows. $^1$H-NMR (DMSO-$d_6$): d 1.92 (m, 1H), 2.09 (m, 1H), 2.30 (s, 3H), 2.50–2.83 (m, 6H), 3.24 (s, 9H), 4.21 (s, 2H), 4.39 (m, 5H), 7.14 (d, 2H), 7.53 (d, 2H), 9.09 (d, 1H).

Example 9

Measurement of Surface Tension Decreasing Ability of Fluorine Compounds and Surfactants A 0.1 weight % aqueous solution was prepared for each of the fluorine compounds of the present invention and the fluorine-containing surfactants for comparison shown in Table 1, and its dynamic surface tension at 100 msec was measured by the maximum bubble pressure method using an automatic dynamic surface tension meter BP-DP3 produced by Kyowa Kaimen Kagaku Co., Ltd. The measured dynamic surface tensions are shown in the following Table 1.

As seen from the results shown in Table 1, it was found that the compounds of the present invention had superior dynamic surface tension decreasing ability.

TABLE 1

Results of surface tension measurement

| Type of surfactant | Dynamic surface tension (mPa/s) | Note |
|---|---|---|
| FS-1 | 65 | Invention |
| FS-47 | 42 | Invention |
| FS-64 | 45 | Invention |
| Comparative Compound FC-1 | 56 | Comparative |
| Comparative Compound FC-2 | 65 | Comparative |
| Comparative Compound FC-3 | 65 | Comparative |
| Comparative Compound FC-4 | 55 | Comparative |
| Comparative Compound FC-5 | 55 | Comparative |

Comparative Compound FC-1

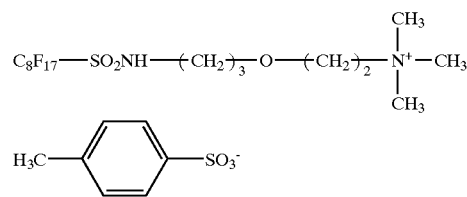

Comparative Compound FC-2

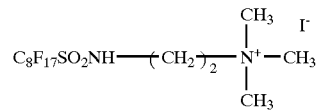

Comparative Compound 3
$C_8H_{17}SO_3K$

Comparative Compound FC-4

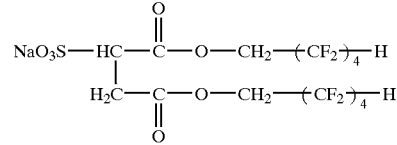

Comparative Compound FC-5

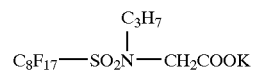

Example 10

Preparation and Evaluation of Silver Halide Color Photographic Light-sensitive Materials (1) Support A support was prepared as follows.
1) First Layer and Undercoat Layer Both surfaces of a polyethylene naphthalate support having a thickness of 90 μm were subjected to a glow discharge treatment with conditions of treatment atmosphere pressure: 2.66×10 Pa, H$_2$O partial pressure in atmosphere gas: 75%, discharge frequency: 30 kHz, output: 2500 W and treatment strength: 0.5 kV·A·min/m². A coating solution having the following composition was coated as the first layer on the above support in a coated amount of 5 mL/m² according to the bar coating method described in JP-B-58-4589.

| | |
|---|---|
| Dispersion of electroconductive microparticles (aqueous dispersion having 10% concentration of $SnO_2/Sb_2O_5$ particles, secondary aggregates having average particle diameter of 0.05 µm composed of primary particles having diameter of 0.005 µm) | 50 weight parts |
| Gelatin | 0.5 weight part |
| Water | 49 weight parts |
| Polyglycerol polyglycidyl ether | 0.16 weight part |
| Polyoxyethylene sorbitan monolaurate (polymerization degree: 20) | 0.1 weight part |

After the first layer was coated on the support, the resultant support was wound around a stainless steel reel having a diameter of 20 cm and subjected to a heat treatment at 110° C. (Tg of the PEN support: 119° C.) for 48 hours in order to give thermal hysteresis to the support to subject it to an annealing treatment. Subsequently, a coating solution having the following composition was coated on the surface of the support opposite to the surface coated with the first layer by the bar coating method in a coating amount of 10 mL/m² as an undercoat layer for a silver halide emulsion.

| | |
|---|---|
| Gelatin | 1.01 weight part |
| Salicylic acid | 0.30 weight part |
| Resorcin | 0.40 weight part |
| Polyoxyethylene nonyl phenyl ether (polymerization degree: 10) | 0.11 weight part |
| Water | 3.53 weight parts |
| Methanol | 84.57 weight parts |
| n-Propanol | 10.08 weight parts |

Further, a second layer and third layer were successively coated on the first layer.

2) Second Layer (i) Dispersion of Magnetic Substance

To an open-type kneader, 1100 weight parts of Co-coated γ-Fe₂O₃ magnetic substance (average length of the longer axis: 0.25 µm, $S_{BET}$: 39 m²/g, Hc: 6.56×10⁴ A/m, ss: 77.1 Am²/kg, sr: 37.4 Am²/kg), 220 weight parts of water and 165 weight parts of a silane coupling agent [3-(polyoxyethynyl)oxypropyltrimethoxysilane (polymerization degree: 10)] were added and well kneaded for 3 hours. The roughly dispersed viscous dispersion was dried at 70° C. for 24 hours to remove water and then subjected to a heat treatment at 110° C. for 1 hour to prepare surface-treated magnetic particles.

Further, a mixture having the following composition was kneaded again in an open-type kneader for 4 hours.

| | |
|---|---|
| Surface-treated magnetic particles mentioned above | 855 g |
| Diacetyl cellulose | 25.3 g |
| Methyl ethyl ketone | 136.3 g |
| Cyclohexanone | 136.3 g |

Further, a mixture having the following composition was finely dispersed in a sand mill (¼ G) at 2000 rpm for 4 hours. As media, glass beads having a diameter of 1 mm φ were used.

| | |
|---|---|
| Kneaded mixture mentioned above | 45 g |
| Diacetyl cellulose | 23.7 g |
| Methyl ethyl ketone | 127.7 g |
| Cyclohexanone | 127.7 g |

Further, a magnetic substance-containing intermediate mixture was prepared with the following composition.

(ii) Preparation of Magnetic Substance-containing Intermediate Dispersion

| | |
|---|---|
| Finely dispersed magnetic substance mixture mentioned above | 674 g |
| Diacetyl cellulose solution (solid content: 4.34%, solvent: methyl ethyl ketone/cyclohexanone = 1/1) | 24280 g |
| Cyclohexanone | 46 g |

These were mixed and then stirred by Disper to prepare a "magnetic substance-containing intermediate dispersion".

An a-alumina abrasive dispersion was prepared with the following composition.

(a) Preparation of Sumicorundum AA-1.5 Particle Dispersion (Average Primary Particle Diameter: 1.5 µm, Specific Surface Area: 1.3 m²/g)

| | |
|---|---|
| Sumicorundum AA-1.5 | 152 g |
| Silane coupling agent KBM 903 (Shinetsu Silicone Co.) | 0.48 g |
| Diacetyl cellulose solution (solid content 4.5%, solvent: methyl ethyl ketone/cyclohexanone = 1/1) | 227.52 g |

The mixture having the above composition was finely dispersed in a ceramic-coated sand mill (¼ G) at 800 rpm for 4 hours. As media, zirconia beads having a diameter of 1 mm F were used.

(b) Colloidal Silica Particle Dispersion (Microparticles)

"MEK-ST" manufactured by Nissan Chemical Industries Ltd. was used.

This was a dispersion of colloidal silica having average primary particle diameter of 0.015 µm in methyl ethyl ketone as a dispersion medium and had a solid content of 30%.

(iii) Preparation of Second Layer Coating Solution

| | |
|---|---|
| Magnetic substance-containing intermediate dispersion mentioned above | 19053 g |
| Diacetyl cellulose solution (solid content 4.5%, solvent: methyl ethyl ketone/cyclohexanone = 1/1) | 264 g |
| Colloidal silica dispersion [MEK-ST] [Dispersion b] (solid content 30%) | 128 g |
| AA-1.5 dispersion [Dispersion a] | 12 g |
| Millionate MR-400 (manufactured by Nippon Polyurethane Co., Ltd.) diluted solution (solid content 20%, diluting solvent: methyl ethyl ketone/cyclohexanone = 1/1) | 203 g |
| Methyl ethyl ketone | 170 g |
| Cyclohexanone | 170 g |

The coating solution obtained by mixing and stirring the above was coated in a coating amount of 29.3 mL/m² by means of a wire bar. Drying of the coated layer was performed at 110° C. The thickness of the dried magnetic layer was 1.0 μm.

3) Third Layer (Higher Fatty Acid Ester Lubricant-containing Layer)

(i) Preparation of Lubricant Stock Dispersion

The following Solution A was heated for dissolution, added to Solution B and then dispersed by a high pressure homogenizer to prepare a stock dispersion of lubricant.

| Solution A | |
|---|---|
| Compound shown below $C_6H_{13}CH(OH)(CH_2)_{10}COOC_{50}H_{101}$ | 399 weight parts |
| Compound shown below $n\text{-}C_{50}H_{101}O(CH_2CH_2O)_{16}H$ | 171 weight parts |
| Cyclohexanone | 830 weight parts |
| Solution B | |
| Cyclohexanone | 8600 weight parts |

(ii) Preparation of Spherical Inorganic Particle Dispersion

Spherical inorganic particle dispersion [c1] was prepared with the following composition.

| | |
|---|---|
| Isopropyl alcohol | 93.54 weight parts |
| Silane coupling agent KBM 903 (Shinetsu Silicone Co.) Compound 1-1: $(CH_3O)_3Si\text{—}(CH_2)_3\text{—}NH_2$ | 5.53 weight parts |
| Compound 1 | 2.93 weight parts |
| Seahostar KEP 50 (amorphous spherical silica, average particle diameter: 0.5 μm, Nippon Shokubai Co., Ltd) | 88.00 weight parts |

Compound 1

$$\begin{array}{c} \text{nC}_4\text{H}_9\text{—}\underset{\underset{C_2H_5}{|}}{CH}\text{—}CH_2O\overset{\overset{O}{\|}}{C}\text{—}CH\text{—}SO_3Na \\ \text{nC}_4\text{H}_9\text{—}\underset{\underset{C_2H_5}{|}}{CH}\text{—}CH_2O\overset{\overset{\|}{O}}{C}\text{—}CH_2 \end{array}$$

The mixture having the above composition was stirred for 10 minutes and further added with the following.
Diacetone alcohol 252.93 weight parts The above mixture was dispersed with cooling on ice and stirring for 3 hour by using an ultrasonic wave homogenizer "SONIFIER 450 (BRANSON Co., Ltd.)" to obtain Spherical inorganic particle dispersion c1.

(iii) Preparation of Spherical Organic Polymer Particle Dispersion

Spherical organic polymer particle dispersion [c2] was prepared with the following composition.

| | |
|---|---|
| XC99-A8808 (spherical crosslinked polysiloxane particles, average particle diameter: 0.9 μm, Toshiba Silicone Co., Ltd.) | 60 parts by weight |
| Methyl ethyl ketone | 120 parts by weight |
| Cyclohexanone (solid content 20%, solvent: methyl ethyl ketone/cyclohexanone = 1/1) | 120 parts by weight |

A mixture of the above was dispersed with cooling on ice and stirring for 2 hours by using the ultrasonic wave homogenizer "SONIFIER 450 (BRANSON Co., Ltd.)" to obtain Spherical organic polymer particle dispersion c2.

(iv) Preparation of Coating Solution for Third Layer

The following components were added to 542 g of the aforementioned lubricant stock dispersion to obtain a coating solution for third layer.

| | |
|---|---|
| Diacetone alcohol | 5950 g |
| Cyclohexanone | 176 g |
| Ethyl acetate | 1700 g |
| Seahostar KEP 50 dispersion [c1] mentioned above | 53.1 g |
| Spherical polymer particle dispersion [c2] mentioned above | 300 g |
| Megafack F-178K (Dainippon Ink and Chemicals, solid content: 30%) | 4.8 g |
| BYK 310 (BYK Chemi Japan Co., Ltd., solid content 25%) | 5.3 g |

The above coating solution for third layer was coated on the second layer in a coating amount of 10.35 mL/m² and dried at 110° C. and then at 97° C. for 3 minutes.

(2) Coating of Light-sensitive Layer

Then, layers having the following compositions were coated as stacked layers on the undercoat layer side of the above support to prepare a color negative film.

(Compositions of Light-sensitive Layers)

Major materials used in the layers are classified as follows.

ExC: Cyan coupler
ExM: Magenta coupler
ExY: Yellow coupler
UV: Ultraviolet absorber
HBS: High boiling point organic solvent
H: Gelatin hardener Specific compounds are identified with any of the above abbreviations followed by numeral, and chemical formulas thereof are mentioned below.

The numerical figures given to the components indicate coating amounts in a unit of g/m². With respect to silver halide, the coating amount is indicated in terms of silver.

First Layer (1st Antihalation Layer)

| | | |
|---|---|---|
| Black colloidal silver | Silver | 0.122 |
| Silver bromide (0.07 μm) emulsion | Silver | 0.01 |
| Gelatin | | 0.919 |
| ExM-1 | | 0.066 |
| ExC-1 | | 0.002 |
| ExC-3 | | 0.002 |
| Cpd-2 | | 0.001 |
| F-8 | | 0.010 |
| HBS-1 | | 0.005 |
| HBS-2 | | 0.002 |

Second Layer (2nd Antihalation Layer)

| | | |
|---|---|---|
| Black colloidal silver | Silver | 0.055 |
| Gelatin | | 0.425 |
| ExF-1 | | 0.002 |
| F-8 | | 0.012 |
| Solid disperse dye ExF-7 | | 0.120 |
| HBS-1 | | 0.074 |

Third Layer (Intermediate Layer)

| | |
|---|---|
| ExC-2 | 0.050 |
| Cpd-1 | 0.090 |
| Polyethyl acrylate latex | 0.200 |
| HBS-1 | 0.100 |
| Gelatin | 0.700 |

Fourth Layer (Low Sensitivity Red-sensitive Emulsion Layer)

| | | |
|---|---|---|
| Em-D | Silver | 0.577 |
| Em-C | Silver | 0.347 |
| ExC-1 | | 0.188 |
| ExC-2 | | 0.011 |
| ExC-3 | | 0.075 |
| ExC-4 | | 0.121 |
| ExC-5 | | 0.010 |
| ExC-6 | | 0.007 |
| ExC-8 | | 0.050 |
| ExC-9 | | 0.020 |
| Cpd-2 | | 0.025 |
| Cpd-4 | | 0.025 |
| HBS-1 | | 0.114 |
| HBS-5 | | 0.038 |
| Gelatin | | 1.474 |

Fifth Layer (Medium Sensitivity Red-sensitive Emulsion Layer)

| | | |
|---|---|---|
| Em-B | Silver | 0.431 |
| Em-C | Silver | 0.432 |
| ExC-1 | | 0.154 |
| ExC-2 | | 0.068 |
| ExC-3 | | 0.018 |
| ExC-4 | | 0.103 |
| ExC-5 | | 0.023 |
| ExC-6 | | 0.010 |
| ExC-8 | | 0.016 |
| ExC-9 | | 0.005 |
| Cpd-2 | | 0.036 |
| Cpd-4 | | 0.028 |
| HBS-1 | | 0.129 |
| Gelatin | | 1.086 |

Sixth Layer (High Sensitivity Red-sensitive Emulsion Layer)

| | | |
|---|---|---|
| Em-A | Silver | 1.108 |
| ExC-1 | | 0.180 |
| ExC-3 | | 0.035 |
| ExC-6 | | 0.029 |
| ExC-8 | | 0.110 |
| ExC-9 | | 0.020 |
| Cpd-2 | | 0.064 |
| Cpd-4 | | 0.077 |
| HBS-1 | | 0.329 |
| HBS-2 | | 0.120 |
| Gelatin | | 1.245 |

Seventh Layer (Intermediate Layer)

| | |
|---|---|
| Cpd-1 | 0.094 |
| Cpd-6 | 0.369 |
| Solid disperse dye ExF-4 | 0.030 |
| HBS-1 | 0.049 |
| Polyethyl acrylate latex | 0.088 |
| Gelatin | 0.886 |

Eighth Layer (Layer Imparting Interlayer Effect to Red-sensitive Layer)

| | | |
|---|---|---|
| Em-J | Silver | 0.293 |
| Em-K | Silver | 0.293 |
| Cpd-4 | | 0.030 |
| ExM-2 | | 0.120 |
| ExM-3 | | 0.016 |
| ExM-4 | | 0.026 |
| ExY-1 | | 0.016 |
| ExY-4 | | 0.036 |
| ExC-7 | | 0.026 |
| HBS-1 | | 0.090 |
| HBS-3 | | 0.003 |
| HBS-5 | | 0.030 |
| Gelatin | | 0.610 |

Ninth Layer (Low Sensitivity Green-sensitive Emulsion Layer)

| | | |
|---|---|---|
| Em-H | Silver | 0.329 |
| Em-G | Silver | 0.333 |
| Em-I | Silver | 0.088 |
| ExM-2 | | 0.378 |
| ExM-3 | | 0.047 |
| ExY-1 | | 0.017 |
| ExC-7 | | 0.007 |
| HBS-1 | | 0.098 |
| HBS-3 | | 0.010 |
| HBS-4 | | 0.077 |
| HBS-5 | | 0.548 |
| Cpd-5 | | 0.010 |
| Gelatin | | 1.470 |

Tenth Layer (Medium Sensitivity Green-sensitive Emulsion Layer)

| | | |
|---|---|---|
| Em-F | Silver | 0.457 |
| ExM-2 | | 0.032 |
| ExM-3 | | 0.029 |
| ExM-4 | | 0.029 |
| ExY-3 | | 0.007 |
| ExC-6 | | 0.010 |
| ExC-7 | | 0.012 |
| ExC-8 | | 0.010 |
| HBS-1 | | 0.065 |
| HBS-3 | | 0.002 |
| HBS-5 | | 0.020 |
| Cpd-5 | | 0.004 |
| Gelatin | | 0.446 |

Eleventh Layer (High Sensitivity Green-sensitive Emulsion Layer)

| | | |
|---|---|---|
| Em-E | Silver | 0.794 |
| ExC-6 | | 0.002 |
| ExC-8 | | 0.010 |
| ExM-1 | | 0.013 |
| ExM-2 | | 0.011 |
| ExM-3 | | 0.030 |

-continued

| | |
|---|---|
| ExM-4 | 0.017 |
| ExY-3 | 0.003 |
| Cpd-3 | 0.004 |
| Cpd-4 | 0.007 |
| Cpd-5 | 0.010 |
| HBS-1 | 0.148 |
| HBS-5 | 0.037 |
| Polyethyl acrylate latex | 0.099 |
| Gelatin | 0.939 |

Twelfth Layer (Yellow Filter Layer)

| | |
|---|---|
| Cpd-1 | 0.094 |
| Solid disperse dye ExF-2 | 0.150 |
| Solid disperse dye ExF-5 | 0.010 |
| Oil soluble dye ExF-6 | 0.010 |
| HBS-1 | 0.049 |
| Gelatin | 0.630 |

Thirteenth Layer (Low Sensitivity Blue-sensitive Emulsion Layer)

| | | |
|---|---|---|
| Em-O | Silver | 0.112 |
| Em-M | Silver | 0.320 |
| Em-N | Silver | 0.240 |
| ExC-1 | | 0.027 |
| ExC-7 | | 0.013 |
| ExY-1 | | 0.002 |
| ExY-2 | | 0.890 |
| ExY-4 | | 0.058 |
| Cpd-2 | | 0.100 |
| Cpd-3 | | 0.004 |
| HBS-1 | | 0.222 |
| HBS-5 | | 0.074 |
| Gelatin | | 2.058 |

Fourteenth Layer (High Sensitivity Blue-sensitive Emulsion Layer)

| | | |
|---|---|---|
| Em-L | Silver | 0.714 |
| ExY-2 | | 0.211 |
| ExY-4 | | 0.068 |
| Cpd-2 | | 0.075 |
| Cpd-3 | | 0.001 |
| HBS-1 | | 0.071 |
| Gelatin | | 0.678 |

Fifteenth Layer (1st Protective Layer)

| | | |
|---|---|---|
| Silver iodobromide (0.07 $\mu$m) emulsion | Silver | 0.301 |
| UV-1 | | 0.211 |
| UV-2 | | 0.132 |
| UV-3 | | 0.198 |
| UV-4 | | 0.026 |
| F-11 | | 0.009 |
| S-1 | | 0.086 |
| HBS-1 | | 0.175 |
| HBS-4 | | 0.050 |
| Gelatin | | 1.984 |

Sixteenth Layer (2nd Protective Layer)

| | |
|---|---|
| H-1 | 0.400 |
| B-1 (diameter: 0.8 $\mu$m) | 0.050 |
| B-2 (diameter: 3.0 $\mu$m) | 0.150 |
| B-3 (diameter: 3.0 $\mu$m) | 0.050 |
| S-1 | 0.200 |
| Gelatin | 0.750 |
| W-1 | 0.056 |

Furthermore, W-1 to W-4, B-4 to B-6, F-1 to F-19, lead salt, platinum salt, iridium salt and rhodium salt were optionally added to the layers in order to improve storage stability, process property, pressure durability, antifungal and antibacterial properties, antistatic property and coating property.

Preparation of Dispersion of Organic Solid Disperse Dye ExF-2 of the twelfth layer was dispersed as follows.

| | |
|---|---|
| Wet cake of ExF-2 (containing 17.6 weight % of water) | 2.800 kg |
| Sodium octylphenyldiethoxymethane-sulfonate (31 weight % aqueous solution) | 0.376 kg |
| F-15 (7% aqueous solution) | 0.011 kg |
| Water | 4.020 kg |
| Total | 7.210 kg |
| (adjusted to pH = 7.2 with NaOH) | |

Slurry having the above composition was roughly dispersed by stirring using a dissolver and further dispersed by using an agitator mill LMK-4 at a peripheral speed of 10 m/s, discharge rate of 0.6 kg/minute and zirconia bead (diameter: 0.3 mm) charging ratio of 80% until the relative absorbance of the dispersion became 0.29 to obtain solid microparticle dispersion. The mean particle size of the dye microparticles was 0.29 $\mu$m.

Similarly, solid dispersions of ExF-4 and ExF-7 were obtained. The mean particle sizes of dye microparticles were 0.28 $\mu$m and 0.49 $\mu$m, respectively. ExF-5 was dispersed by the microprecipitation dispersion method described in EP549489A, Example 1. The mean particle size was 0.06 $\mu$m.

TABLE 2

| Emulsion | Average content of silver iodide (mol %) | Diameter as sphere ($\mu$m) | Aspect ratio | Diameter as circle ($\mu$m) | Grain thickness ($\mu$m) | Shape |
|---|---|---|---|---|---|---|
| Em-A | 4 | 0.92 | 14 | 2 | 0.14 | Tabular |
| Em-B | 5 | 0.8 | 12 | 1.6 | 0.13 | Tabular |
| Em-C | 4.7 | 0.51 | 7 | 0.85 | 0.12 | Tabular |
| Em-D | 3.9 | 0.37 | 2.7 | 0.4 | 0.15 | Tabular |
| Em-E | 5 | 0.92 | 14 | 2 | 0.14 | Tabular |
| Em-F | 5.5 | 0.8 | 12 | 1.6 | 0.13 | Tabular |
| Em-G | 4.7 | 0.51 | 7 | 0.85 | 0.12 | Tabular |
| Em-H | 3.7 | 0.49 | 3.2 | 0.58 | 0.18 | Tabular |
| Em-I | 2.8 | 0.29 | 1.2 | 0.27 | 0.23 | Tabular |
| Em-J | 5 | 0.8 | 12 | 1.6 | 0.13 | Tabular |
| Em-K | 3.7 | 0.47 | 3 | 0.53 | 0.18 | Tabular |
| Em-L | 5.5 | 1.4 | 9.8 | 2.6 | 0.27 | Tabular |
| Em-M | 8.8 | 0.64 | 5.2 | 0.85 | 0.16 | Tabular |
| Em-N | 3.7 | 0.37 | 4.6 | 0.55 | 0.12 | Tabular |
| Em-O | 1.8 | 0.19 | — | — | — | Cubic |

In Table 2, Emulsions Em-A to Em-C were added with optimum amounts of Spectral sensitization dyes 1–3 and optimally sensitized by gold sensitization, sulfur sensitization and selenium sensitization. Emulsion Em-J was added with optimum amounts of Spectral sensitization dyes 7 and 8 and optimally sensitized by gold sensitization, sulfur sensitization and selenium sensitization. Emulsion Em-L was added with optimum amounts of Spectral sensitization dyes 9–11 and optimally sensitized by gold sensitization, sulfur sensitization and selenium sensitization. Emulsion Em-L was added with optimum amounts of Spectral sensitization dyes 10–12 and optimally sensitized by gold sensitization and sulfur sensitization. Emulsions Em-D, Em-H, Em-I, Em-K, Em-M and Em-N were added with optimum amounts of spectral sensitization dyes shown in Table 3 and optimally sensitized by gold sensitization, sulfur sensitization and selenium sensitization.

TABLE 3

| Emulsion | Spectral sensitization dye | Added amount (mol/mol of silver) |
|---|---|---|
| Em-D | Spectral sensitization dye 1 | $5.44 \times 10^{-4}$ |
| | Spectral sensitization dye 2 | $2.35 \times 10^{-4}$ |
| | Spectral sensitization dye 3 | $7.26 \times 10^{-6}$ |
| Em-H | Spectral sensitization dye 8 | $6.52 \times 10^{-4}$ |
| | Spectral sensitization dye 13 | $1.35 \times 10^{-4}$ |
| | Spectral sensitization dye 6 | $2.48 \times 10^{-5}$ |
| Em-I | Spectral sensitization dye 8 | $6.09 \times 10^{-4}$ |
| | Spectral sensitization dye 13 | $1.26 \times 10^{-4}$ |
| | Spectral sensitization dye 6 | $2.32 \times 10^{-5}$ |
| Em-K | Spectral sensitization dye 7 | $6.27 \times 10^{-4}$ |
| | Spectral sensitization dye 8 | $2.24 \times 10^{-4}$ |
| Em-M | Spectral sensitization dye 9 | $2.43 \times 10^{-4}$ |
| | Spectral sensitization dye 10 | $2.43 \times 10^{-4}$ |
| | Spectral sensitization dye 11 | $2.43 \times 10^{-4}$ |
| Em-N | Spectral sensitization dye 9 | $3.28 \times 10^{-4}$ |
| | Spectral sensitization dye 10 | $3.28 \times 10^{-4}$ |
| | Spectral sensitization dye 11 | $3.28 \times 10^{-4}$ |

The sensitizing dyes mentioned in Table 3 are illustrated below.

Sensitizing Dye 1

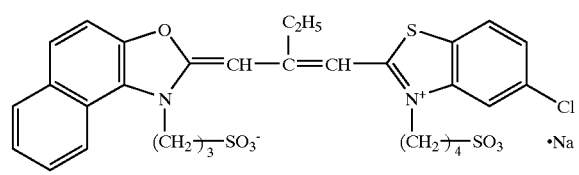

Sensitizing Dye 2

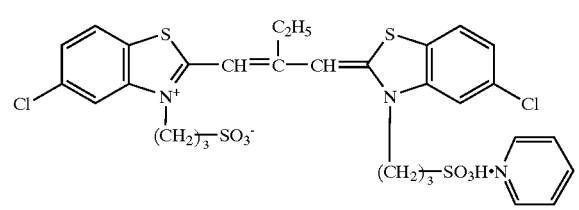

Sensitizing Dye 3

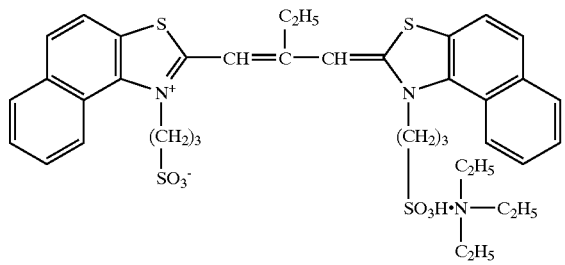

Sensitizing Dye 4

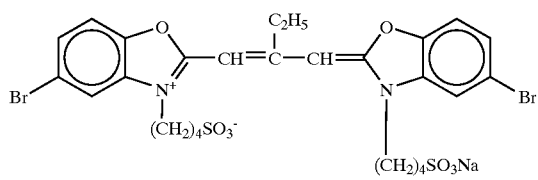

Sensitizing Dye 5

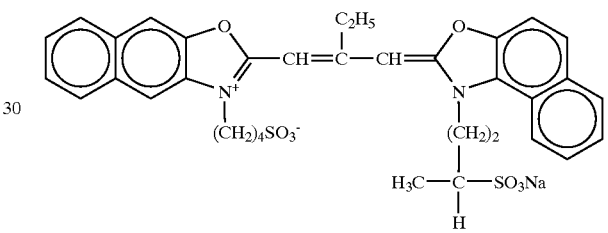

Sensitizing Dye 6

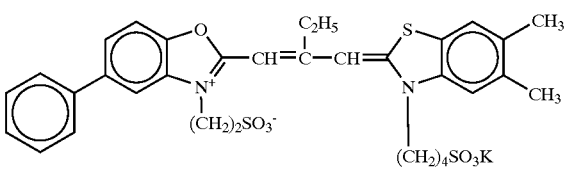

Sensitizing Dye 7

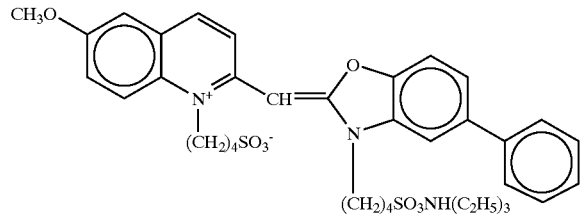

Sensitizing Dye 8

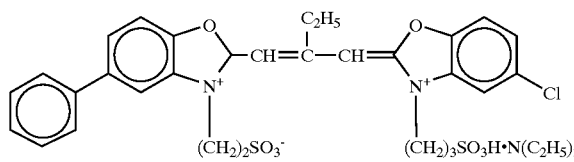

Sensitizing Dye 9

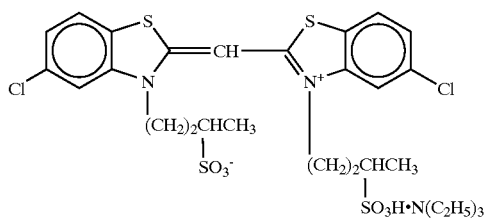

Sensitizing Dye 10

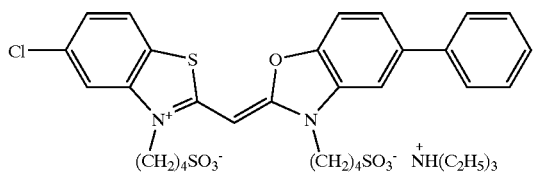

Sensitizing Dye 11

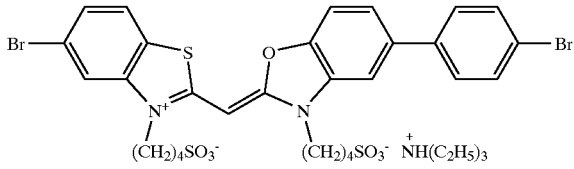

Sensitizing Dye 12

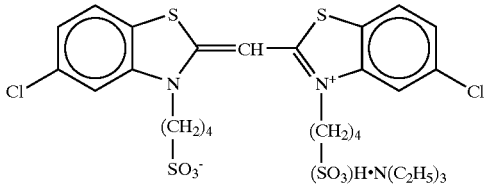

Sensitizing Dye 13

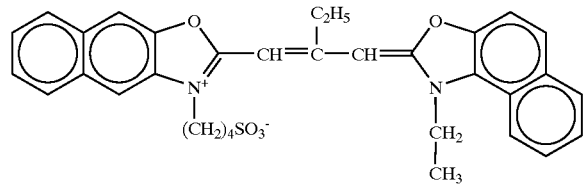

For the preparation of tabular grains, low molecular weight gelatin was used according to the example of JP-A-1-158426. Emulsions Em-A to Em-K contained optimum amounts of Ir and Fe. Emulsions Em-L to Em-O were subjected to reduction sensitization during the grain formation. When the tabular grains were observed with a high voltage electron microscope, dislocation lines were observed as described in JP-A-3-237450. As for Emulsions Em-A to Em-C and Em-J, dislocation was introduced by using an iodide ion-releasing agent according to the example of JP-A-6-11782. As for Emulsion Em-E, dislocation was introduced by using silver iodide fine grains prepared immediately before addition in a separate chamber equipped with a magnetic coupling induction type stirring machine described in JP-A-10-43570.

The compounds used for the layers are mentioned below.

ExC-1

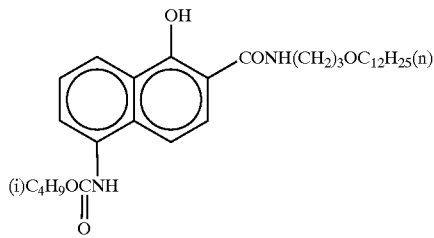

ExC-2

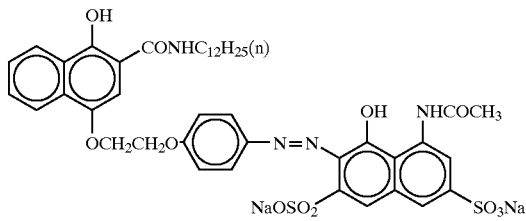

ExC-3

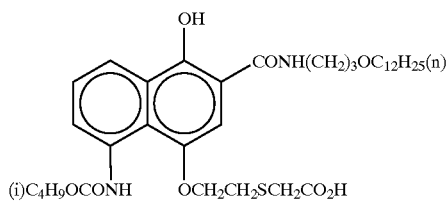

ExC-4

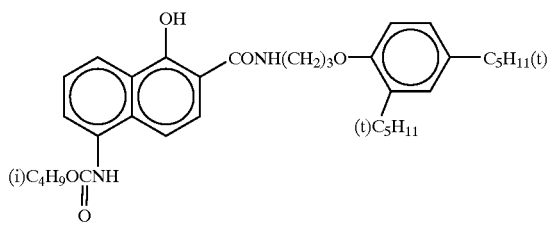

ExC-5
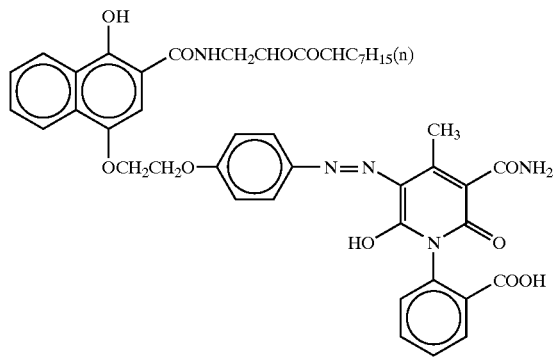
ExC-6
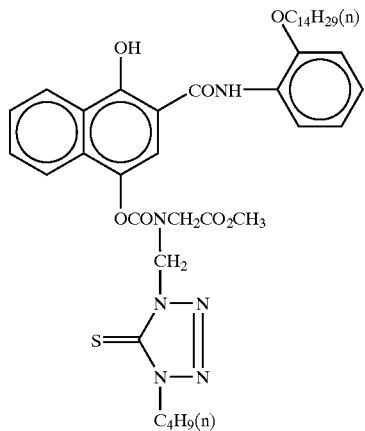
ExC-7
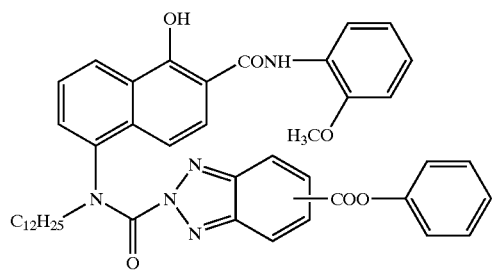
ExC-8
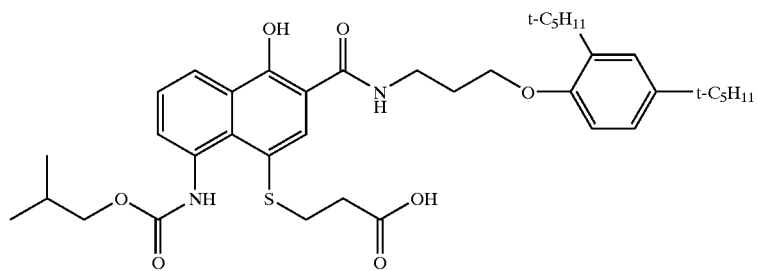
ExC-9
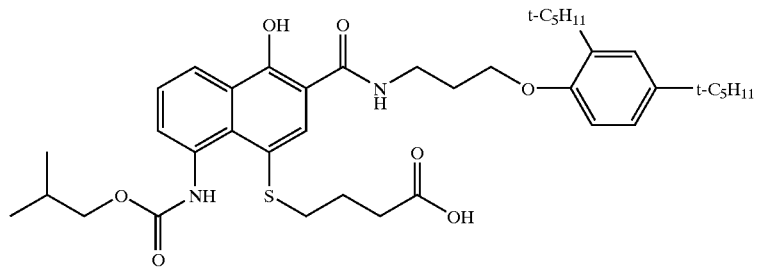

ExM-1
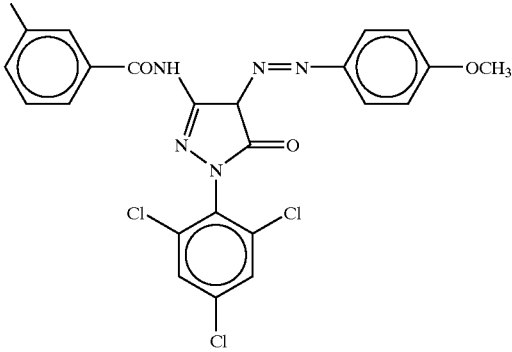
ExM-2
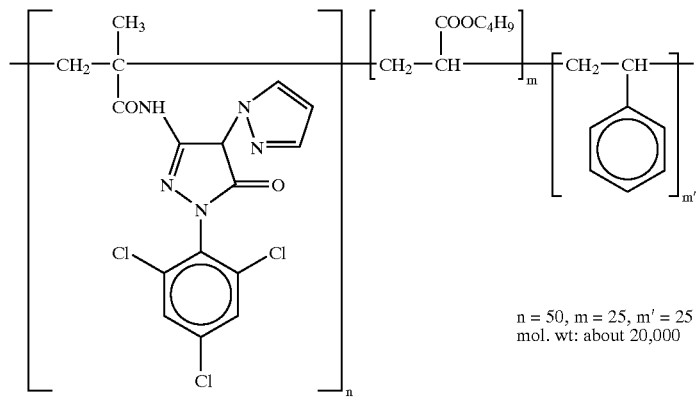
n = 50, m = 25, m' = 25
mol. wt: about 20,000
ExM-3
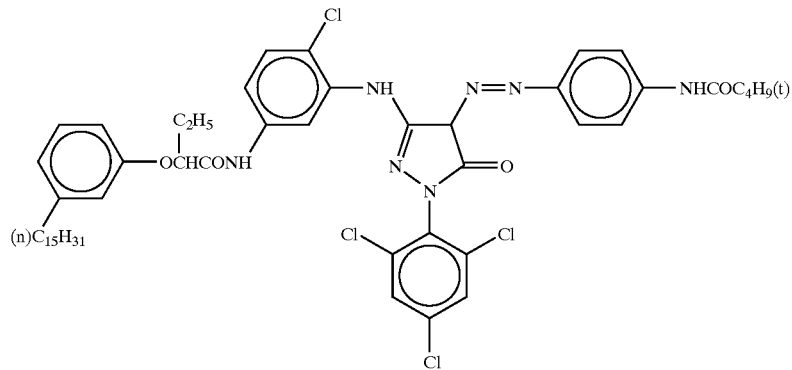
ExM-4
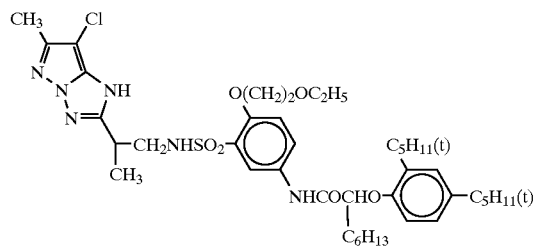
ExY-1
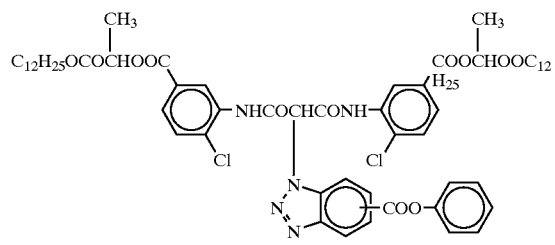

-continued
ExY-2
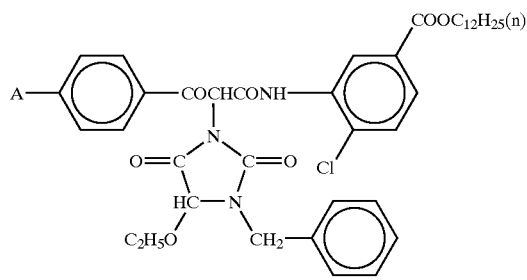
ExY-3
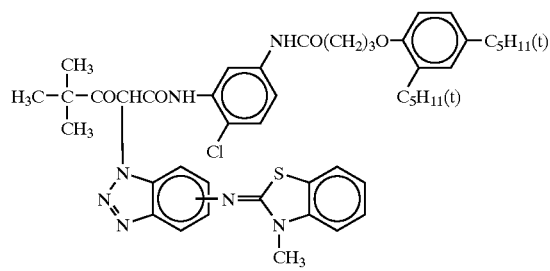
ExY-4
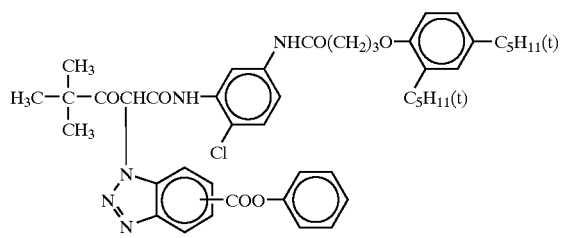
Cpd-1
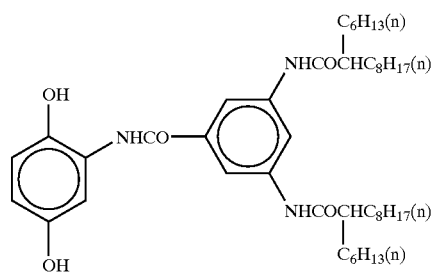
Cpd-2
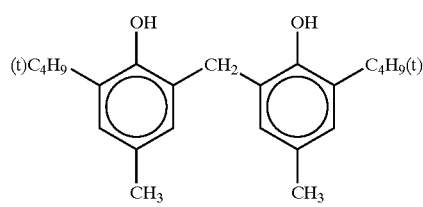
Cpd-3
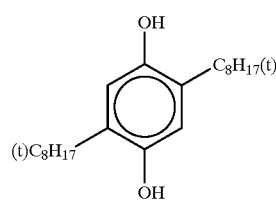
Cpd-4
(n)$C_{14}H_{29}OCOCH_2CH_2CONOH$
　　　　　　　　　　$CH_3$
Cpd-5
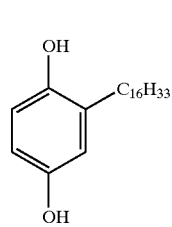
Cpd-6
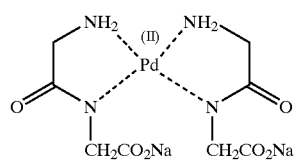
UV-1
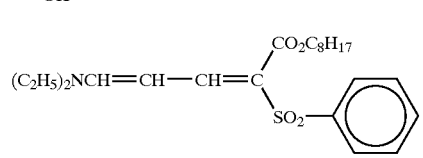
UV-2
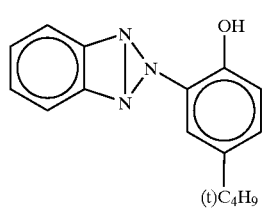
UV-3
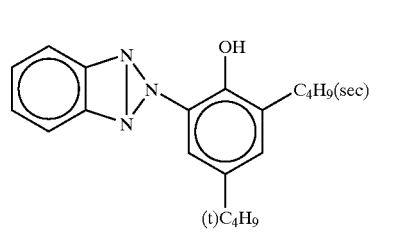
UV-4
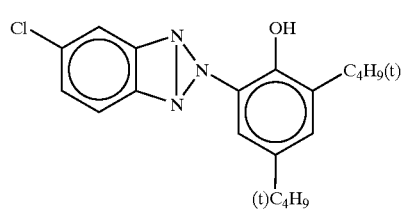
B-1
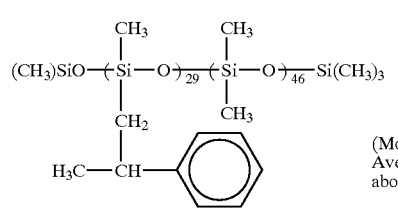
(Molar ratio)
Average molecular weight: about 8,000

-continued
B-2 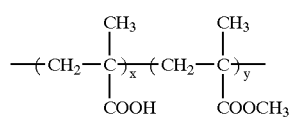 x/y = 40/60 (weight ratio)
Average molecular weight: about 20,000
B-3 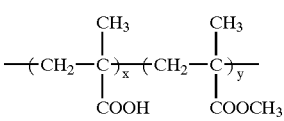 x/y = 10/90 (weight ratio)
Average molecular weight: about 35,000
HBS-1 Tricresyl phosphate
HBS-2 Di-n-butyl phthalate
HBS-3 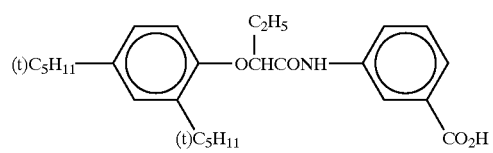
HBS-4 Tri(2-ethylhexyl) phosphate
HBS-5 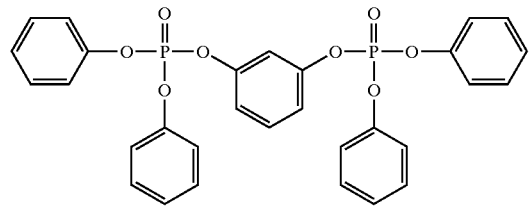
S-1 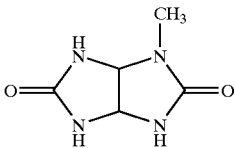
H-1 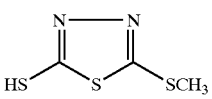
F-1 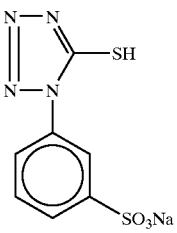
F-2 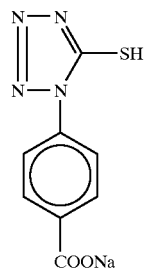
F-3 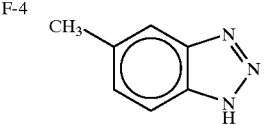
F-4 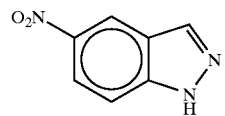
F-5 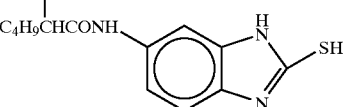
F-6 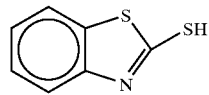
F-7 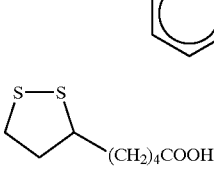
F-8 
F-9 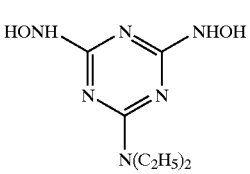
F-10 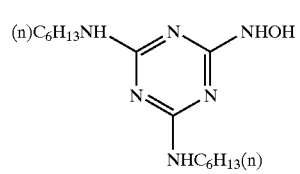
F-11 (in image)

-continued
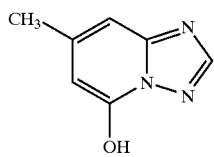 F-12
 F-13
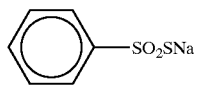 F-14
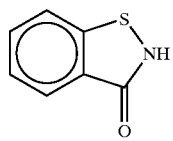 F-15
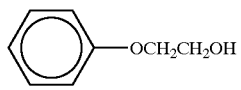 F-16
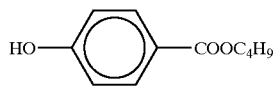 F-17
 F-18
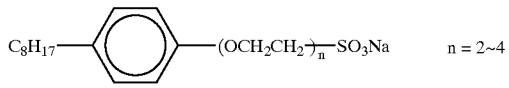 F-19
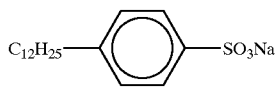 W-2
n = 2~4
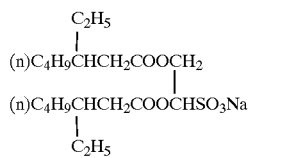 W-1
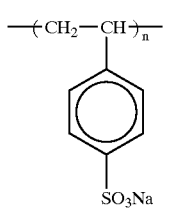 W-3
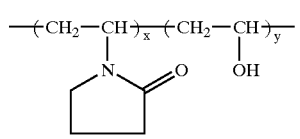 W-4
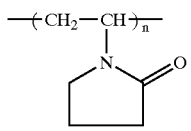 B-4
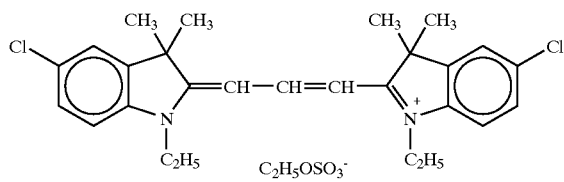 B-5
Average molecular weight: about 750,000
x/y = 70/30 (weight ratio)
Average molecular weight: about 17,000
B-6
ExF-1
Average molecular weight: about 10,000

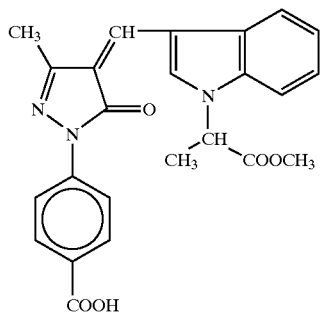

ExF-2

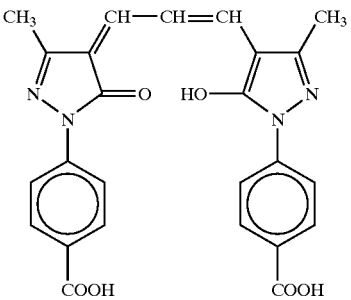

ExF-4

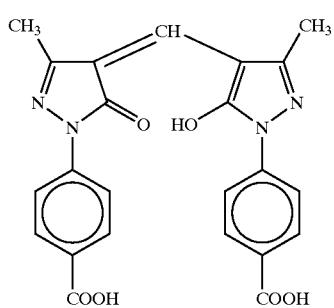

ExF-5

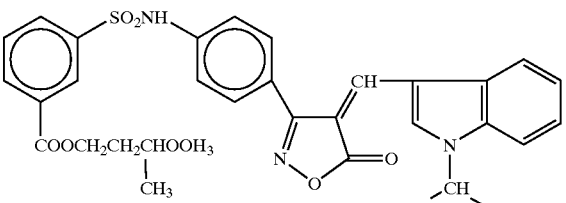

ExF-6

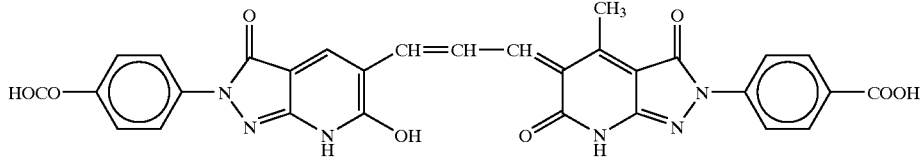

ExF-7

The aforementioned silver halide color photographic light-sensitive material was designated as Sample 100.

In addition to Sample 100, Sample 101 was prepared in the same manner as that for Sample 100 except that the surfactant of the present invention, FS-1, was added to the sixteenth layer in an amount of 0.008 g/m². Samples 102, 103 and 109–114 according to the present invention and Comparative Samples 104–108 were prepared, which each contained, instead of FS-1, each of the surfactants shown in Table 4 in such an amount that the amount added to each layer should be the same amount as that of FS-1 in the sixteenth layer of Sample 101 in terms of the fluorine amount.

<Evaluation>

(1) Electrification Controlling Ability Test

Electrification controlling ability of the produced Samples 100–114 was evaluated. As for two sheets of each sample in a size of 35 mm×120 mm, surfaces opposite to the surfaces coated with emulsions were adhered with a double-sided adhesive tape, nipped and transported between earthed facing rollers wound with nylon ribbons in an environment at a temperature of 25° C. and relative humidity of 10%. Then, they were entered into a Faraday cage to measure electrification quantity. The results of the measurement of electrification quantity are each indicated with an electrification sequence index. The electrification sequence index is a value calculated by multiplying by $10^9$ a value obtained by subtracting electrification quantity of each of Samples 101–114 from that of Sample 100. A sample showing an electrification sequence index of less than −1.0 was determined to have sufficient electrification sequence controlling ability.

The results are shown in Table 4. As clearly seen from the results shown in Table 4, it was found that, among conventional fluorine-containing surfactants, only those having a long chain perfluoroalkyl group showed the electrification controlling ability, but a compound having a short fluorinated alkyl group having less than 6 carbon atoms (Comparative Compound FC-4) showed insufficient electrification controlling ability. On the other hand, it became clear that the compounds of the present invention had sufficient electrification controlling ability although they had a short fluorinated alkyl group.

Further, surfaces of the samples according to the present invention were analyzed by XPS (X-ray photoelectron spectroscopy) to quantify F atom/carbon atom ratio on the surfaces. As a result, good correlation was observed between the electrification controlling ability and the surface fluorine amount, and thus it was found that the fluorine compounds of the present invention effectively distribute fluorine atoms on the sample surfaces.

TABLE 4

Results of electrification controlling ability test

| Type of surfactant | | Electrification sequence index | Electrification sequence controlling ability | Note |
|---|---|---|---|---|
| Sample 101 | FS-1 | −3.1 | Observed | Invention |
| Sample 102 | FS-47 | −2.3 | Observed | Invention |
| Sample 103 | FS-64 | −2.3 | Observed | Invention |
| Sample 104 | Comparative Compound FC-1 | −4.6 | Observed | Comparative |

TABLE 4-continued

Results of electrification controlling ability test

| | Type of surfactant | Electrification sequence index | Electrification sequence controlling ability | Note |
|---|---|---|---|---|
| Sample 105 | Comparative Compound FC-2 | −3.0 | Observed | Comparative |
| Sample 106 | Comparative Compound FC-3 | −2.0 | Observed | Comparative |
| Sample 107 | Comparative Compound FC-4 | −0.5 | Not observed | Comparative |
| Sample 108 | Comparative Compound FC-5 | −2.3 | Observed | Comparative |
| Sample 109 | FS-7 | −3.1 | Observed | Invention |
| Sample 110 | FS-13 | −3.1 | Observed | Invention |
| Sample 112 | FS-16 | −2.3 | Observed | Invention |
| Sample 113 | FS-70 | −3.0 | Observed | Invention |
| Sample 114 | FS-71 | −2.2 | Observed | Invention |

(2) Evaluation of Repelling Characteristic

Samples 201–208 shown in Table 5 were produced, which contained the same components as Samples 101–108, respectively, except that the particle diameter of B-1 contained in each sixteenth layer of Samples 101–108 was changed to 3 μm and all of the fluorine-containing surfactants were added in the same amount as that used in Sample 101. Samples 201–208 were prepared by coating the layers by the slide bead coating method at a rate of 1 m/second and immediately drying them. Then, number of repelling portions observed on the coated surface was counted by visual inspection, and repelling degree was calculated based on the counted number. The repelling degree used herein means a percentage of a number of repelling portions of each sample with respect to the number of repelling portions observed in Sample 208, and a sample showing a repelling degree of 100 or less was determined to have repelling inhibition effect.

The results are shown in Table 5 mentioned below.

TABLE 5

Results of evaluation for repelling characteristic

| | Type of surfactant | Repelling degree | Dynamic surface tension (mPa/s) | Note |
|---|---|---|---|---|
| Sample 201 | FS-1 | 90 | 65 | Invention |
| Sample 202 | FS-47 | 10 | 42 | Invention |
| Sample 203 | FS-64 | 30 | 45 | Invention |
| Sample 204 | Comparative Compound FC-1 | 100 | 56 | Comparative |
| Sample 205 | Comparative Compound FC-2 | 140 | 65 | Comparative |
| Sample 206 | Comparative Compound FC-3 | 150 | 65 | Comparative |
| Sample 207 | Comparative Compound FC-4 | 6 | 52 | Comparative |
| Sample 208 | Comparative Compound FC-5 | 100 | 55 | Comparative |

It was demonstrated that all the surfactants of the present invention had superior ability to reduce generation of repelling and, as shown by the results together with the results of Example 1, the dynamic surface tension values of the aqueous solutions and the repelling degree showed good correlation.

Furthermore, considering the results shown in Table 4 together, it is clear that the surfactants of the present invention are more excellent in reconciliation of the charge controlling ability and the reduction of repelling compared with the comparative compounds.

(3) Photographic Characteristics

Samples 101 to 108 were left under conditions of a temperature 40° C. and a relative humidity of 70% for 14 hours, then exposed for 1/100 second through a continuous wedge at a color temperature of 4800°K and subjected to the color development processing described below. Density of color observed in the samples after the processing was measured by using a blue filter to evaluate photographic performance. Sensitivity was evaluated with a relative value of logarithm of reciprocal of exposure (lux·second) that gave a yellow density equal to fog density plus 0.2. All of the materials had similar photographic characteristics including sensitivity, color image density etc.

The development was performed as follows by using a FP-360B automatic processor manufactured by Fuji Photo Film Co., Ltd.

However, the FP-360B was modified such that the overflow solution of the bleaching bath should be entirely discharged to a waste solution tank without being supplied to the subsequent bath. This FP-360B was provided with evaporation correcting means described in JIII Journal of Technical Disclosure No. 94-4992.

The processing steps and the processing solution compositions are shown below.

(Processing Steps)

| Step | Processing time | Processing temperature | Replenishing amount* | Tank volume |
|---|---|---|---|---|
| Color development | 3 minute and 5 seconds | 37.8° C. | 20 mL | 11.5 L |
| Bleaching | 50 seconds | 38.0° C. | 5 mL | 5 L |
| Fixing (1) | 50 seconds | 38.0° C. | — | 5 L |
| Fixing (2) | 50 seconds | 38.0° C. | 8 mL | 5 L |
| Washing with water | 30 seconds | 38.0° C. | 17 mL | 3 L |
| Stabilization (1) | 20 seconds | 38.0° C. | — | 3 L |
| Stabilization (2) | 20 seconds | 38.0° C. | 15 mL | 3 L |
| Drying | 1 minute and 30 seconds | 60.0° C. | | |

*Replenishing amount per 1.1 m of light-sensitive material having a width of 35 mm (equivalent to one 24 Ex. film)

The stabilizer and fixer were counterflowed from (2) to (1), and the overflow of washing water was entirely introduced into the fixing bath (2). The amounts of the developer, bleaching solution and fixer carried over to the bleaching step, fixing step and washing step were 2.5 mL, 2.0 mL and 2.0 mL, respectively, per 1.1 m of light-sensitive material having a width of 35 mm. Each crossover time was 6 seconds, and this time was included in the processing time of each preceding step.

The aperture areas of the processor were 100 cm$^2$ for the color developer, 120 cm$^2$ for the bleaching solution and about 100 cm$^2$ for the other processing solutions.

The compositions of the processing solutions are shown below.

| (Color developer) | Tank Solution (g) | Replenisher (g) |
|---|---|---|
| Diethylenetriaminepentaacetic acid | 3.0 | 3.0 |
| Disodium cathecol-3,5-Disulfonate | 0.3 | 0.3 |
| Sodium sulfite | 3.9 | 5.3 |
| Potassium carbonate | 39.0 | 39.0 |
| Disodium-N,N-bis-(2-sulfonato-ethyl)hydroxylamine | 1.5 | 2.0 |
| Potassium bromide | 1.3 | 0.3 |
| Potassium iodide | 1.3 mg | — |
| 4-Hydroxy-6-methyl-1,3,3a,7-tetrazaindene | 0.05 | — |
| Hydroxylamine sulfate | 2.4 | 3.3 |
| 2-Methyl-4-[N-ethyl-N-(β-hydroxyethyl)amino]aniline sulfate | 4.5 | 6.5 |
| Water to make | 1.0 L | 1.0 L |
| pH (adjusted with potassium hydroxide and sulfuric acid) | 10.05 | 10.18 |

| (Bleaching solution) | Tank Solution (g) | Replenisher (g) |
|---|---|---|
| Ferric ammonium 1,3-diaminopropane-tetraacetate monohydrate | 113 | 170 |
| Ammonium bromide | 70 | 105 |
| Ammonium nitrate | 14 | 21 |
| Succinic acid | 34 | 51 |
| Maleic acid | 28 | 42 |
| Water to make | 1.0 L | 1.0 L |
| pH (adjusted with aqueous ammonia) | 4.6 | 4.0 |

(Fixing (1) Tank Solution)

Mixture of the above bleaching tank solution and the following fixing tank solution (5:95 (volume ratio), pH 6.8).

| (Fixing (2)) | Tank Solution (g) | Replenisher (g) |
|---|---|---|
| Aqueous ammonium thiosulfate solution (750 g/L) | 240 mL | 720 mL |
| Imidazole | 7 | 21 |
| Ammonium methanethiosulfonate | 5 | 15 |
| Ammonium methanesulfinate | 10 | 30 |
| Ethylenediaminetetraacetic acid | 13 | 39 |
| Water to make | 1.0 L | 1.0 L |
| pH (adjusted with aqueous ammonia and acetic acid) | 7.4 | 7.45 |

(Washing Water)

Tap water was applied to a mixed-bed column filled with an H type strongly acidic cation exchange resin (Amberlite IR-120B, Rohm & Haas Co.) and an OH type strongly basic anion exchange resin (Amberlite IR-400) to make its concentrations of calcium and magnesium to be 3 mg/L or less. Subsequently, 20 mg/L of sodium dichloroisocyanurate and 150 mg/L of sodium sulfate were added. The pH of the solution was in the range of 6.5–7.5.

(Stabilization Solution)
This solution was commonly used for the tank solution and the replenisher.

| | (unit: g) |
|---|---|
| Sodium p-toluenesulfinate | 0.03 |
| Polyoxyethylene p-mononylphenyl ether (average polymerization degree: 10) | 0.2 |
| 1,2-Benzoisothiazolin-3-one sodium | 0.10 |
| Disodium ethylenediaminetetraacetate | 0.05 |
| 1,2,4-Triazole | 1.3 |
| 1,4-Bis(1,2,4-triazol-1-yl-methyl)-piperazine | 0.75 |
| Water to make | 1.0 L |
| pH 8.5 | |

As explained above, the compounds of the present invention shows superior surface orientation property and enables formation of uniform coated films when they are used for forming coated films. According to the present invention, there can also be provided coating compositions that enable formation of uniform coating films having antistatic property. Furthermore, according to the present invention, there can be provided silver halide photographic light-sensitive materials that can be stably produced and are imparted with antistatic property.

What is claimed is:

1. A silver halide photographic light-sensitive material having one or more layers including a light-sensitive silver halide emulsion layer on a support, wherein any of the layers contains a compound represented by the following formula (1):

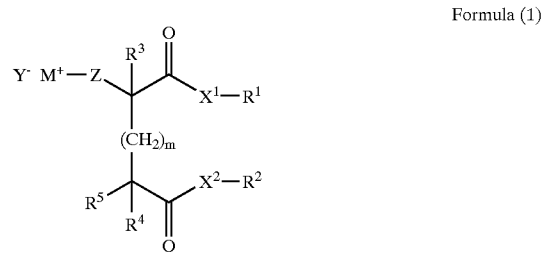

Formula (1)

wherein $R^1$ and $R^2$ each represent a substituted or unsubstituted alkyl group provided that at least one of $R^1$ and $R^2$ represents an alkyl group substituted with one or more fluorine atoms; $R^3$, $R^4$ and $R^5$ each independently represent a hydrogen atom or a substituent; $X^1$, $X^2$ and Z each independently represent a divalent bridging group or a single bond; $M^+$ represents a cationic substituent; $Y^-$ represents a counter anion, but $Y^-$ may not be present when the intramolecular charge excluding $Y^-$ is 0; and m is 0 or 1.

2. The silver halide photographic light-sensitive material according to claim 1, which has a light-insensitive hydrophilic colloid layer as an outermost layer and contains a compound represented by the aforementioned formula (1) in the outermost layer.

3. The silver halide photographic light-sensitive material according to claim 2, which further contains an anionic or nonionic surfactant other than the compound represented by the aforementioned formula (1) in the outermost layer.

4. The silver halide photographic light-sensitive material according to claim 1, wherein the compound represented by the aforementioned formula (1) is a compound represented by the following general formula (1-a):

Formula (1-a)

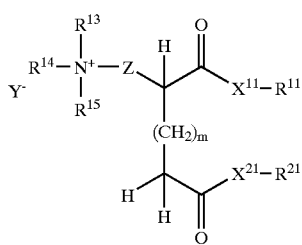

Formula (1-c)

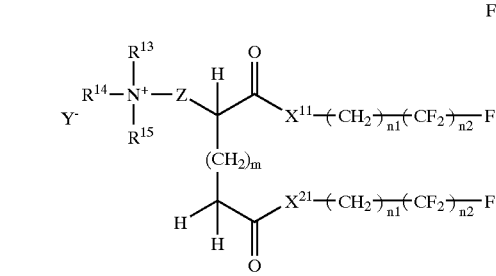

wherein $R^{11}$ and $R^{21}$ each represent a substituted or unsubstituted alkyl group provided that at least one of $R^{11}$ and $R^{21}$ represents an alkyl group substituted with one or more fluorine atoms and the total carbon atom number of $R^{11}$ and $R^{21}$ is 19 or less; $R^{13}$, $R^{14}$ and $R^{15}$ each independently represent a substituted or unsubstituted alkyl group and two or more of $R^{13}$, $R^{14}$ and $R^{15}$ may be taken together with the nitrogen atom to which $R^{13}$, $R^{14}$ and $R^{15}$ bond to form a ring; $X^{11}$ and $X^{21}$ each independently represent —O—, —S— or —$NR^{31}$— where $R^{31}$ represents a hydrogen atom or a substituent; Z represents a divalent bridging group or a single bond; $Y^-$ represents a counter anion, but $Y^-$ may not be present when the intramolecular charge excluding $Y^-$ is 0; and m is 0 or 1.

5. The silver halide photographic light-sensitive material according to claim 1, wherein the compound represented by the aforementioned formula (1) is a compound represented by the following general following formula (1-b):

Formula (1-b)

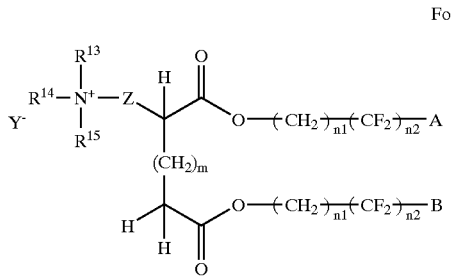

wherein $R^{13}$, $R^{14}$ and $R^{15}$ each independently represent a substituted or unsubstituted alkyl group and two or more of $R^{13}$, $R^{14}$ and $R^{15}$ may be taken together with the nitrogen atom to which $R^{13}$, $R^{14}$ and $R^{15}$ bond to form a ring; Z represents a divalent bridging group, and A and B each represents a fluorine atom or a hydrogen atom; $n^1$ represents an integer of 1–6 and $n^2$ represents an integer of 3–8; $Y^-$ represents a counter anion, but $Y^-$ may not be present when the intramolecular charge excluding $Y^-$ is 0; and m is 0 or 1.

6. The silver halide photographic light-sensitive material according to claim 1, wherein the compound represented by the aforementioned formula (1) is a compound represented by the following general following formula (1-c):

wherein $n^1$ represents an integer of 1–6 and $n^2$ represents an integer of 3–8 provided that $2(n^1+n^2)$ is 19 or less; $R^{13}$, $R^{14}$ and $R^{15}$ each independently represent a substituted or unsubstituted alkyl group and two or more of $R^{13}$, $R^{14}$ and $R^{15}$ may be taken together with the nitrogen atom to which $R^{13}$, $R^{14}$ and $R^{15}$ bond to form a ring; $X^{11}$ and $X^{21}$ each independently represent —O—, —S— or —$NR^{31}$— where $R^{31}$ represents a hydrogen atom or a substituent; Z represents a divalent bridging group or a single bond; $Y^-$ represents a counter anion, but $Y^-$ may not be present when the intramolecular charge excluding $Y^-$ is 0; and m is 0 or 1.

7. The silver halide photographic light-sensitive material according to claim 1, wherein the silver halide emulsion layer contains an emulsion in which 50% or more of total projected area of silver halide grains is provided by tabular grains having an aspect ratio of 3 or more.

8. The silver halide photographic light-sensitive material according to claim 5, wherein $n^2$ in the formula (1-b) represents an integer of 3–6.

9. The silver halide photographic light-sensitive material according to claim 6, wherein $n^1$ in the formula (1-c) represents 2 or 3.

10. The silver halide photographic light-sensitive material according to claim 6, wherein $n^2$ in the formula (1-c) represents an integer of 3–6.

11. The silver halide photographic light-sensitive material according to claim 1, wherein $M^+$ in the formula (1) is an organic cationic group.

12. The silver halide photographic light-sensitive material according to claim 11, wherein the organic cationic group has a nitrogen atom or a phosphorus atom.

13. The silver halide photographic light-sensitive material according to claim 11, wherein the organic cationic group is a pyridinium cation or an ammonium cation.

14. The silver halide photographic light-sensitive material according to claim 11, wherein the organic cationic group is represented by the following formula (2)

Formula (2)

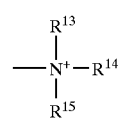

in which $R^{13}$, $R^{14}$ and $R^{15}$ each independently represent a substituted or unsubstituted alkyl group and two or more of $R^{13}$, $R^{14}$ and $R^{15}$ may be taken together with the nitrogen atom to which $R^{13}$, $R^{14}$ and $R^{15}$ bond to form a ring.

* * * * *